United States Patent
Fu

(10) Patent No.: US 9,528,157 B2
(45) Date of Patent: Dec. 27, 2016

(54) METHODS, COMPOSITIONS, AND KITS FOR DETERMING THE PRESENCE/ABSENCE OF A VARIANT NUCLEIC ACID SEQUENCE

(75) Inventor: Guoliang Fu, Abingdon (GB)

(73) Assignee: GENEFIRST LIMITED, Abingdon, Oxford (GB)

( * ) Notice: Subject to any disclaimer, the term of this patent is extended or adjusted under 35 U.S.C. 154(b) by 99 days.

(21) Appl. No.: 13/979,480

(22) PCT Filed: Jan. 16, 2012

(86) PCT No.: PCT/GB2012/000037
§ 371 (c)(1),
(2), (4) Date: Sep. 24, 2013

(87) PCT Pub. No.: WO2012/095639
PCT Pub. Date: Jul. 19, 2012

(65) Prior Publication Data
US 2014/0017685 A1    Jan. 16, 2014

(30) Foreign Application Priority Data

Jan. 14, 2011 (GB) .................................. 1100620.2
May 12, 2011 (GB) .................................. 1107940.7

(51) Int. Cl.
*C12Q 1/68*    (2006.01)

(52) U.S. Cl.
CPC ........... *C12Q 1/6883* (2013.01); *C12Q 1/6827* (2013.01); *C12Q 1/6853* (2013.01)

(58) Field of Classification Search
None
See application file for complete search history.

(56) References Cited

U.S. PATENT DOCUMENTS

| | | | |
|---|---|---|---|
| 5,595,890 A | 1/1997 | Newton et al. | |
| 5,891,625 A | 4/1999 | Buchardt et al. | |
| 7,803,543 B2 | 9/2010 | Chiou et al. | |
| 8,815,515 B1* | 8/2014 | Zhou ...................... | C12Q 1/686 435/6.1 |
| 2004/0014105 A1 | 1/2004 | Schroeder et al. | |
| 2004/0091905 A1 | 5/2004 | Guo | |
| 2010/0009355 A1* | 1/2010 | Kolodney .......................... | 435/6 |
| 2010/0112557 A1* | 5/2010 | Tobler .................. | C12Q 1/6848 435/5 |
| 2010/0221717 A1* | 9/2010 | Chen .................... | C12Q 1/6858 435/6.14 |

FOREIGN PATENT DOCUMENTS

| | | |
|---|---|---|
| EP | 2314680 | 4/2011 |
| EP | 2646576 | 10/2013 |
| WO | 2007106534 | 9/2007 |
| WO | 2007149903 | 12/2007 |
| WO | 2008043987 | 4/2008 |
| WO | 2009/053679 | 4/2009 |
| WO | 2011146403 | 11/2011 |

OTHER PUBLICATIONS

Pont-Kingdon et al. (Direct molecular haplotyping by melting curve analysis of hybridization probes: beta 2-adrenergic receptor haplotypes as an example, Nucleic Acids Res. Jun. 3, 2005;33(10):e89).*
Merriam-Webster, Definition of "middle," accessed Apr. 2, 2015, available at http://www.merriam-webster.com/dictionary/middle.*
Erali et al. (High Resolution Melting Applications for Clinical Laboratory Medicine, Exp Mol Pathol. Aug. 2008 ; 85(1): 50-58).*
Belousov et al. (Single nucleotide polymorphism genotyping by two colour melting curve analysis using the MGB EclipseTM Probe System in challenging sequence environment, Hum Genomics. Mar. 2004;1(3):209-17).*
Gundry et al. (Amplicon Melting Analysis with Labeled Primers: A Closed-Tube Method for Differentiating Homozygotes and Heterozygotes, Clin Chem. Mar. 2003;49(3):396-406).*
Morlan et al. (Mutation Detection by Real-Time PCR: A Simple, Robust and Highly Selective Method, PLoS One. 2009;4(2):e4584. Epub Feb. 25, 2009).*
Margraf et al. (Masking Selected Sequence Variation by Incorporating Mismatches Into Melting Analysis Probes, Hum Mutat. Mar. 2006;27(3):269-78).*
Orou et al. (Allele-Specific Competitive Blocker PCR: A One-Step Method With Applicability to Pool Screening, Hum Mutat. 1995;6(2):163-9).*
Zhou et al. (Rare allele enrichment and detection by allele-specific PCR, competitive probe blocking, and melting analysis, BioTechniques, vol. 50, No. 5, May 2011, pp. 311-318).*
Urata et al. (High-Sensitivity Detection of the A3243G Mutation of Mitochondrial DNA by a Combination of Allele-Specific PCR and Peptide Nucleic Acid-Directed PCR Clamping, Clinical Chemistry 50:11 2045-2051 (2004)).*
GeneFirst KRAS-HiFi-Melt Mutation Test Kit information Leaflet, Apr. 2014.
GeneFirst Detection of K-Ras mutations using KRAS-HiFi-Melt assay, Internal Standard Operating Procedure Doc, May 30, 2013. Unpublished schematic (sent to EPO Sep. 2, 2014).
Mancini et al., "The use of COLD-PCR and high-resolution melting analysis improves the limit of detection of KRAS amd BRAF mutation in colorectal cancer", The Journal of Molecular Diagnostics: JMD, Sep. 2010, vol. 12, No. 5, Sep. 2010, pp. 705-711 ISSN 1943-7811.
Morlan et al., "Mutation detection by real-time PCR: a simple, robust and highly selective method", PLOS One, 2009, vol. 4, No. 2, p. e4584, ISSN: 1932-6203.

(Continued)

*Primary Examiner* — Aaron Priest
(74) *Attorney, Agent, or Firm* — Michael Best & Friedrich LLP

(57) ABSTRACT

The present invention provides methods, compositions and kits for detecting the presence, absence or amount of a target nucleic acid or at least one variant nucleotide in one or more nucleic acids contained in a sample.

4 Claims, 4 Drawing Sheets

(56) References Cited

OTHER PUBLICATIONS

Bernard et al. "Homogeneous Multiplex Genotyping of Hemochromatosis Mutations with Fluorescent Hybridization Probes," (1998), Am. J. Pathol., 153: 1055-1061.

Chen et al. "Rapid Detection of K-ras Mutations in Bile by Peptide Nucleic Acid-mediated PCR Clamping and Melting Curve Analysis: Comparison with Restriction Fragment Length Polymorphism Analysis," 2004, Clinical Chemistry 50:3, 481-489.

Dabritz et al. "Detection of Ki-ras mutations in tissue and plasma samples of patients with pancreatic cancer using PNA-mediated PCR clamping and hybridisation probes," 2005, Br. J. Cancer, 92, 405-412.

Demers et al., "Biochemical Markers of Bone Turnover in Patients with Metastatic Bone Disease," 1995, Clin. Chem. 41/10, 1489-1494.

Demers et al., "Enhanced PCR amplification of VNTR locus D1S80 using peptide nucleic acid (PNA)," Nucleic Acids Research, 1995, vol. 23, No. 15, 3050-3055.

Erali et al., "SNP Genotyping by Unlabeled Probe Melting Analysis," Ale:hod5 in Molecular Biology, vol. 429, 2008, 199-206.

Gibson NJ, "The use of real-time PCR methods in DNA sequence variation analysis," 2006, Clin Chim Acta. 363 (1-2):32-47.

Jeffreys et al., "DNA Enrichment by Allele-Specific Hybridization (DEASH): A Novel Method for Haplotyping and for Detecting Low-Frequency Base Substitutional Variants and Recombinant DNA Molecules," 2003 Genome Res. 13 (10):2316-2324.

Kreuzer et al., "Preexistence and evolution of imatinib mesylate-resistant clones in chronic myelogenous leukemia detected by a PNA-based PCR clamping technique," Ann Hematol (2003) 82:284-289.

Laughlin et al., "Rapid Method for Detection of Mutations in the Nucleophosmin Gene in Acute Myeloid Leukemia," Journal of Molecular Diagnostics, vol. 10, No. 4, Jul. 2008, 338-345.

Lay, et al. "Real-time fluorescence genotyping of factor V Leiden during rapid-cycle PCR," (1997), Clin. Chem., 43 :2262-2267.

Letsinger et al., "Cationic Oligonucleotides," 1988, J. Amer. Chem. Soc. 110:4470-4471.

Luo et al., "Detection of rare mutant K-ras DNA in a single-tube reaction using peptide nucleic acid as both PCR clamp and sensor probe," Nucleic Acid Res. 2006, vol. 34, No. 2, e12, 1-7.

Lyon et al., "LightCycler Technology in Molecular Diagnostics," Journal of Molecular Diagnostics, vol. 11, No. 2, Mar. 2009, 93-101.

Miyazawa et al., "Effect of PTK/ZK on the Angiogenic Switch in Head and Neck Tumors," J Dent Res. Dec. 2008 ; 87(12): 1166-1171.

Nagai et al., "Genetic Heterogeneity of the Epidermal Growth Factor Receptor in Non-Small Cell Lung Cancer Cell Lines Revealed by a Rapid and Sensitive Detection System, the Peptide Nucleic Acid-Locked Nucleic Acid PCR Clamp," Cancer Res 2005;65:7276-7282.

Newton et al., "Analysis of any point mutation in DNA. The amplification refractory mutation system (ARMS)," Nucleic Acids Res. 17:2503-2516, 1989.

Orum et al., "Single base pair mutation analysis by PNA directed PCR clamping," Nucleic Acids Research, 1993, vol. 21, No. 23, 5332-5336.

Ren et al., "Rapid and sensitive detection of hepatitis B virus 1762T/1764A double mutation from hepatocellular carcinomas using LNAmediated PCR clamping and hybridization probes," J Virol Methods, Jun. 2009, 158(1-2): 24-29.

Senescau et al., "Use of a Locked-Nucleic-Acid Oligomer in the Clamped-Probe Assay for Detection of a Minority Pfcrt K76T Mutant Population of Plasmodium falciparum," Journal of Clinical Microbiology, Jul. 2005, p. 3304-3308.

Taback et al., "Circulating DNA Microsatellites: Molecular Determinants of Response to Biochemotherapy in Patients With Metastatic Melanoma," J Natl Cancer Inst. Jan. 21, 2004; 96(2): 152-156.

Wang et al. "Comparison of bisulfite modification of 5-methyldeoxycytidine and deoxycytidine residues," (1980), Nucleic Acids Res., 8, 4777-4790.

Seyama T et al., A novel blocker-PCR method for detection of rare mutant alleles in the presence of an excess amount of normal DNA, Nucleic Acids Research, 1992, vol. 20, No. 10 pp. 2493-2496.

\* cited by examiner

SEQUENCE LISTING

<160> NUMBER OF SEQ ID NOS: 25

<210> SEQ ID NO 1
<211> LENGTH: 17
<212> TYPE: DNA
<213> ORGANISM: Artificial Sequence
<220> FEATURE:
<223> OTHER INFORMATION: Primer EGFR21forward1

<400> SEQUENCE: 1
gatcacagat tttgggc                                                  17

<210> SEQ ID NO 2
<211> LENGTH: 18
<212> TYPE: DNA
<213> ORGANISM: Artificial Sequence
<220> FEATURE:
<223> OTHER INFORMATION: Primer EGFR21forward2

<400> SEQUENCE: 2
agatcacaga ttttgggc                                                 18

<210> SEQ ID NO 3
<211> LENGTH: 22
<212> TYPE: DNA
<213> ORGANISM: Artificial Sequence
<220> FEATURE:
<223> OTHER INFORMATION: Primer EGFR21reverse1

<400> SEQUENCE: 3
ctttgcctcc ttctgcatgg ta                                            22

<210> SEQ ID NO 4
<211> LENGTH: 24
<212> TYPE: DNA
<213> ORGANISM: Artificial Sequence
<220> FEATURE:
<223> OTHER INFORMATION: Primer EGFR21reverse2

<400> SEQUENCE: 4
ctccttactt tgcctccttc tgca                                          24

<210> SEQ ID NO 5
<211> LENGTH: 26
<212> TYPE: DNA
<213> ORGANISM: Artificial Sequence
<220> FEATURE:
<223> OTHER INFORMATION: Primer EGFR21 probe

<400> SEQUENCE: 5
gatcacaggt tttgctggca aactgc                                        26

<210> SEQ ID NO 6
<211> LENGTH: 50
<212> TYPE: DNA
<213> ORGANISM: Artificial Sequence
<220> FEATURE:
<223> OTHER INFORMATION: Linked-primer-probe for detecting EGFR exon21
      point mutation L858R

<400> SEQUENCE: 6
ttgatcacag gttttgctgg caaactgcct tgcctccttc tgcatggta               50

<210> SEQ ID NO 7
<211> LENGTH: 19
<212> TYPE: DNA

```
<213> ORGANISM: Artificial Sequence
<220> FEATURE:
<223> OTHER INFORMATION: Primer

<400> SEQUENCE: 7
caatggtagt tggagctgt                                                19

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
gtgttgtggt agttggagct gt                                            22

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
tcagtggtag ttggagctt                                                19

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
caatggtagt tggagctc                                                 18

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
cagaggtagt tggagctga                                                19

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
acagtggtag ttggagcta                                                19

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
aacgatagtt ggagctggtg a                                             21
```

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
caaaggtagt tggagctgc                                              19

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
taagttgtgg tagttggagc tgt                                         23

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
taaggtagtt ggagctggtg a                                           21

<210> SEQ ID NO 17
<211> LENGTH: 25
<212> TYPE: DNA
<213> ORGANISM: Artificial Sequence
<220> FEATURE:
<223> OTHER INFORMATION: Reverse primer

<400> SEQUENCE: 17
ttacctctat tgttggatca tattc                                       25

<210> SEQ ID NO 18
<211> LENGTH: 19
<212> TYPE: DNA
<213> ORGANISM: Artificial Sequence
<220> FEATURE:
<223> OTHER INFORMATION: Blocking probe

<400> SEQUENCE: 18
tggtagttgg ctggtggcg                                              19

<210> SEQ ID NO 19
<211> LENGTH: 18
<212> TYPE: DNA
<213> ORGANISM: Artificial Sequence
<220> FEATURE:
<223> OTHER INFORMATION: Blocking probe

<400> SEQUENCE: 19
ggtagttgga tggtggcg                                               18

<210> SEQ ID NO 20
<211> LENGTH: 21
<212> TYPE: DNA
<213> ORGANISM: Artificial Sequence
<220> FEATURE:

```
<223> OTHER INFORMATION: Detector probe

<400> SEQUENCE: 20
taggcaagag tgccttgacg a                                    21

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
caagatcaca gattttggcg                                      20

<210> SEQ ID NO 22
<211> LENGTH: 19
<212> TYPE: DNA
<213> ORGANISM: Artificial Sequence
<220> FEATURE:
<223> OTHER INFORMATION: Primer

<400> SEQUENCE: 22
gattttgggc tggccaaca                                       19

<210> SEQ ID NO 23
<211> LENGTH: 21
<212> TYPE: DNA
<213> ORGANISM: Artificial Sequence
<220> FEATURE:
<223> OTHER INFORMATION: Reverse primer

<400> SEQUENCE: 23
cttactttgc ctccttctgc a                                    21

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
ccgaagggca tgagctca                                        18

<210> SEQ ID NO 25
<211> LENGTH: 26
<212> TYPE: DNA
<213> ORGANISM: Artificial Sequence
<220> FEATURE:
<223> OTHER INFORMATION: Blocking oligonucleotide

<400> SEQUENCE: 25
gatcacaggt tttgctggca aactgc                               26
```

METHODS, COMPOSITIONS, AND KITS FOR DETERMING THE PRESENCE/ABSENCE OF A VARIANT NUCLEIC ACID SEQUENCE

CROSS-REFERENCE TO RELATED APPLICATIONS

This patent application is a national stage filing under 35 U.S.C. 371 of International Application No. PCT/GB2012/000037, filed on Jan. 16, 2012, which claims foreign priority benefits to United Kingdom Patent Application No. 1100620.2, filed Jan. 14, 2011 and United Kingdom Patent Application No. 1107940.7, filed May 12, 2011, which are incorporated herein by reference in their entireties.

SEQUENCE LISTING

The instant application contains a Sequence Listing which has been submitted in text format via EFS-Web and is hereby incorporated by reference in its entirety. Said text copy, created on Jul. 11, 2013, is named ASFILED_SequenceListing-Text and is 4,880 bytes in size.

BACKGROUND OF THE INVENTION

This invention relates to methods, compositions and kits for determining the presence/absence of a target nucleic acid or one or more variant nucleotide sequences contained in a test sample.

Single nucleotide polymorphisms (SNPs) are the most common type of variation in the human genome. Point mutations are also usually SNPs but the term is normally reserved for those with a low frequency or where there is a known functional, disease-causing role for the variation (Gibson N J, 2006, Clin Chim Acta. 363(1-2):32-47). There are many applications for genotyping polymorphisms and detecting rare mutations. The detection of rare variants is important for the early detection of pathological mutations, particularly in cancer. For instance, detection of cancer-associated point mutations in clinical samples can improve early diagnostics, the identification of minimal residual disease during chemotherapy, determination of personalized therapies and can detect the appearance of tumor cells in relapsing patients. For example, Kras mutation in codons 12 and 13 occurs in 80-90% of pancreatic cancer and 35-50% of colorectal cancer. The measurement of mutation load is also important for the assessment of environmental exposure to mutagens, to monitor endogenous DNA repair, and to study the accumulation of somatic mutations in aging individuals. Additionally, more sensitive and quantitative methods to detect rare variants can revolutionise prenatal diagnosis, enabling the characterization of foetal cells present in maternal blood.

A vast number of methods have been introduced, but no single method has been widely accepted. Many methods for detecting low-frequency variants in genomic DNA use the polymerase chain reaction (PCR) to amplify mutant and wild-type targets. The PCR products are then analysed in a variety of ways, including sequencing, oligonucleotide ligation, restriction digestion, mass spectrometry or hybridization with allele-specific oligonucleotides to identify the variant against the background of wild-type DNA. Other methods use allele-specific PCR to selectively amplify target nucleic acid containing the low-frequency variant, with or without additional selection. For example, by digesting PCR products with a restriction enzyme that specifically cleaves the wild-type product. Current approaches have inherent limitations due to the lack of total specificity of allele-specific primers during PCR, which creates false positives. As a result, all current approaches have limited sensitivity and accuracy (reviewed by Jeffreys A J and May C A, 2003 Genome Res. 13(10):2316-24).

The unifying problem behind all of these PCR approaches for detecting rare variants is replication infidelity during amplification or impreciseness of probe hybridization. This is apparent in a popular mutation detection method described by Newton et al (Nucleic Acids Res. 17:2503-16, 1989; U.S. Pat. No. 5,595,890). This system, an amplification refractory mutation system (ARMS), exploits allele-specific primers that are used for a PCR reaction. This method relies on conditions which permit extension from primers with 3' ends complementary to specific sequence variants, whereas wild-type sequences are not extended. This procedure requires specific primers for each mutation and the PCR conditions are quite rigorous. Mis-priming during amplification often yields inaccurate or misleading results.

Recently, enrichment and detection methods called PNA (or LNA) clamp PCR have been developed (B. Taback et al., 2004; A. Senescau et al., 2005; X David Ren et al., 2009; Todd S. Laughlin et al., 2008; K. Udagawa et al., 2005; Hitoshi Miyazawa, et al., 2008). High affinity nucleic acid analogues such as peptide-nucleic acids (PNAs) are used to inhibit nucleic acid amplification (U.S. Pat. No. 5,891,625, and D. B. Demers et al., 1995, H. Orum et al., 1993)). PNA(LNA)-DNA duplex is more stable than DNA-DNA duplex. Therefore, PNA (or LNA) can specifically block primer annealing or chain extension on a perfectly matched template.

U.S. Pat. No. 7,803,543 discloses a method for determining whether a target polynucleotide sequence contained in a nucleic acid sample has nucleotide variation(s) in a selected region thereof, the steps of which involve the use of a pair of primers that allow the formation of a PCR product which has a sequence covering that of the selected region of the target polynucleotide sequence via a PCR process, and a peptide nucleic acid (PNA) that acts as a PCR clamp as well as a sensor probe. The method uses a first primer which is spaced apart from the 5' end of the sequence of the selected region by 30 nucleotides or more. The PCR process of this method requires that the extension reaction sets to run at a temperature lower than the melting temperature of the perfectly matched probe. This method has a number of drawbacks. The labelled PNA probe is difficult and expensive to synthesize. The method requires an anchor probe which has a high $T_m$ and complicates the reaction and design. If the sample contains the normal target nucleic acid only, the PNA may shut down the reaction, therefore without a separate control, there is no way of knowing if the reaction has worked. This method has poor reproducibility and sensitivity.

US Patent Publication No. 2004/0014105A1 disclose methods for the selective enrichment of low-abundance polynucleotides in a sample. These methods use enzymatically non-extendable nucleobase oligomers to selectively block polymerase activity on high abundance species, thereby resulting in an enrichment of less abundant species in the sample.

US Patent Publication No. 2004/0091905A1 disclose methods for detecting a mutant polynucleotide in a mixture of mutant polynucleotides, wild-type polynucleotides and unrelated polynucleotides. The method uses an extension primer complementary to a first target sequence in both the wild-type and mutant polynucleotides. The method also uses a probe complementary to a second target sequence in the wild-type polynucleotides but not in the mutant polynucleotides. Extension of the primers annealed to the first target sequence in mutant polynucleotides produces long extension products. Extension of the primers annealed to the first target sequence in wild-type polynucleotides is blocked by the probe annealed to the second target sequence. Short extension products or no extension products are produced. The extension products are isolated and used in a polymerase chain reaction (PCR). The PCR preferentially amplifies long extension products.

Lay, et at (Lay, M. J. & Wittwer, C T. (1997), Clin. Chem., 43:2262-2267) reported the use of fluorescent probes and melting curve analysis for genotyping. Hybridization probe coupled with melting curve analysis is widely used for the detection of mutations or SNPs. It usually requires a pair of oligonucleotide probes, the anchor and the sensor (P. S. Bernard et al. (1998), Am. J. Pathol., 153:1055-1061). The anchor and the sensor are labelled with different fluorescent dyes, such that fluorescence energy transfer occurs between the two when they anneal to adjacent sites of a complementary PCR strand. Recent studies using a PNA clamp coupled with a pair of hybridization probes in PCR, demonstrated that homogeneous detection of rare mutations in a closed tube reaction can be achieved (C. Y. Chen et al. 2004; J. Dabritz et al. 2005; K. A. Kreuzer et al. 2003; Y. Nagai et al. 2005). However, in these studies, the PNA competes with the sensor probe for binding to the target nucleic acid. Therefore detection by the melting curve profile is very inefficient. In addition, if more than one variant nucleotide in the same region is expected to be detected, multiple sensor probes have to be designed.

Nevertheless, it will be appreciated that the provision of nucleic acid detection methods that are both accurate and sensitive would provide a contribution to the art.

DETAILED DESCRIPTION

To facilitate an understanding of the invention, a number of terms are defined below.

As used herein, a "sample" refers to any substance containing or presumed to contain nucleic acids and includes a sample of tissue or fluid isolated from an individual or individuals. Particularly, the nucleic acid sample may be obtained from an organism selected from viruses, bacteria, fungi, plants, and animals. Preferably, the nucleic acid sample is obtained from a mammal. In a preferred embodiment of this invention, the mammal is human. The nucleic acid sample can be obtained from a specimen of body fluid or tissue biopsy of a subject, or from cultured cells. The body fluid may be selected from whole blood, serum, plasma, urine, sputum, bile, stool, bone marrow, lymph, semen, breast exudate, bile, saliva, tears, bronchial washings, gastric washings, spinal fluids, synovial fluids, peritoneal fluids, pleural effusions, and amniotic fluid.

As used herein, the term "nucleotide sequence" refers to either a homopolymer or a heteropolymer of deoxyribonucleotides, ribonucleotides or other nucleic acids.

As used herein, the term "nucleotide" generally refers to the monomer components of nucleotide sequences even though the monomers may be nucleoside and/or nucleotide analogs, and/or modified nucleosides such as amino modified nucleosides in addition to nucleotides. In addition, "nucleotide" includes non-naturally occurring analog structures.

As used herein, the term "nucleic acid" refers to at least two nucleotides covalently linked together. A nucleic acid of the present invention will generally contain phosphodiester bonds, although in some cases nucleic acid analogs are included that may have alternate backbones, comprising, for example, phosphoramides, phosphorothioate, phosphorodithioate, O-methylphosphoroamidite linkages, and peptide nucleic acid backbones and linkages. Other nucleic acid analogs include those with positive backbones, non-ionic backbones and non-ribose backbones. Nucleic acids may be single-stranded or double-stranded, as specified, or contain portions of both double-stranded and single-stranded sequence. The nucleic acid may be DNA, both genomic and cDNA, RNA or DNA-RNA hybrids, where the nucleic acid contains any combination of deoxyribo- and ribo-nucleotides, and any combination of bases, including uracil, adenine, thymine, cytosine, guanine, inosine, xathanine, hypoxathanine, etc. Reference to a "DNA sequence" can include both single-stranded and double-stranded DNA. A specific sequence, unless the context indicates otherwise, refers to the single stranded DNA of such sequence, the duplex of such sequence with its complement (double stranded DNA) and/or the complement of such sequence.

As used herein, the "polynucleotide" and "oligonucleotide" are types of "nucleic acid", and generally refer to primers, probes, oligomer fragments to be detected, oligomer controls and unlabelled blocking oligomers and shall be generic to polydeoxyribonucleotides (containing 2-deoxy-D-ribose), polyribonucleotides (containing D-ribose), and any other type of polynucleotide which is an N-glycoside of a purine or pyrimidine base, or modified purine or pyrimidine bases. There is no intended distinction in length between the term "nucleic acid", "polynucleotide" and "oligonucleotide", and these terms will be used interchangeably. "Nucleic acid", "DNA" and similar terms also include nucleic acid analogs. The oligonucleotide is not necessarily physically derived from any existing or natural sequence but may be generated in any manner, including chemical synthesis, DNA replication, reverse transcription or a combination thereof.

When two different, non-overlapping or with some overlapping, oligonucleotides anneal to different regions of the same linear complementary nucleic acid sequence, and the 3' end of one oligonucleotide points toward the 5' end of the other, the former may be called the "upstream" oligonucleotide and the latter the "downstream" oligonucleotide.

As used herein, the terms "target sequence", "target nucleic acid", "target nucleic acid sequence" and "nucleic acids of interest" are used interchangeably and refer to a desired region which is to be either amplified, detected or both, or is the subject of hybridization with a complementary oligonucleotide, polynucleotide, e.g., a blocking oligomer, or the subject of a primer extension process. The target sequence can be composed of DNA, RNA, analogs thereof, or combinations thereof. The target sequence can be single-stranded or double-stranded. In primer extension processes, the target nucleic acid which forms a hybridization duplex with the primer may also be referred to as a "template." A template serves as a pattern for the synthesis of a complementary polynucleotide. A target sequence for use with the present invention may be derived from any living or once living organism, including but not limited to prokaryotes, eukaryotes, plants, animals, and viruses, as well as synthetic and/or recombinant target sequences.

"Primer" as used herein refers to more than one primer and refers to an oligonucleotide, whether occurring naturally or produced synthetically, which is capable of acting as a point of initiation of synthesis when placed under conditions in which synthesis of a primer extension product, which is complementary to a nucleic acid strand is induced i.e., in the presence of nucleotides and an agent for polymerization such as DNA polymerase and at a suitable temperature and in a suitable buffer. Such conditions include the presence of four different deoxyribonucleoside triphosphates and a polymerization-inducing agent such as DNA polymerase or reverse transcriptase, in a suitable buffer ("buffer" includes substituents which are cofactors, or affect pH, ionic strength, etc.), and at a suitable temperature. The primer is preferably single-stranded for maximum efficiency in amplification. The primers herein are selected to be substantially complementary to a strand of each specific sequence to be amplified. This means that the primers must be sufficiently complementary to hybridize with their respective strands. A non-complementary nucleotide fragment may be attached to the 5'-end of the primer, with the remainder of the primer sequence being complementary to the diagnostic section of the target base sequence. Commonly, the primers are complementary, except when non-complementary nucleotides may be present at a predetermined primer terminus as described. In another expression, the primers herein are selected to be substantially identical to a strand of each specific sequence to be amplified. This means that the primers must be sufficiently identical to one strand, so that they can hybridize with their respective other strands.

The complement of a nucleic acid sequence as used herein refers to an oligonucleotide which, when aligned with the nucleic acid sequence such that the 5' end of one sequence is paired with the 3' end of the other, and is in "antiparallel association." Complementarity need not be perfect; stable duplexes may contain mismatched base pairs or unmatched bases.

As used herein, the term "$T_m$" is used in reference to the "melting temperature." The melting temperature is the temperature at which a population of double-stranded polynucleotide molecules or nucleobase oligomers, in homoduplexes or heteroduplexes, become half dissociated into single strands. The equation for calculating the $T_m$ between two molecules takes into account the base sequence as well as other factors including structural and sequence characteristics and the nature of the oligomeric linkages. The melting temperature can be obtained in many ways. For example, the melting temperature can be theoretically determined based on the base length of a duplex, and a mismatch in the duplex will result in a decrease in $T_m$. However, the $T_m$ of a duplex is usually determined experimentally by subjecting a sample of duplexes to a gradual increase in temperature and continuously measuring the dissociation of duplexes into single strands. Methods for determining $T_m$ are well known in the art. For example, $T_m$ may be determined by a shift in UV absorbance, by Surface Plasmon Resonance (SPR), or preferably by fluorescence.

The term "melting profile analysis" or "melting curve analysis" as used herein refers to a procedure for analysing the melting temperatures of an amplified products or a probe hybridised to the amplified products generated from the cycling profile of a PCR process.

As used herein, the term "complementary" refers to the ability of two nucleotide sequences to bind sequence-specifically to each other by hydrogen bonding through their purine and/or pyrimidine bases according to the usual Watson-Crick rules for forming duplex nucleic acid complexes. It can also refer to the ability of nucleotide sequences that may include modified nucleotides or analogues of deoxyribonucleotides and ribonucleotides to bind sequence-specifically to each other by other than the usual Watson Crick rules to form alternative nucleic acid duplex structures.

The term "identical" means that two nucleic acid sequences have the same sequence or a complementary sequence. "Identical" and "complementary", sometimes, mean the same thing.

For example, there is a diagnostic region in a target nucleic acid sequence which contains variant nucleotides. This diagnostic region is a double-stranded region in a DNA fragment. A probe targeting this diagnostic region is complementary to one strand of the diagnostic region, but is identical to the other strand of the diagnostic region.

For purposes of the present invention, the term "substantially complementary" or "substantially identical" means that the primer or probe must be sufficiently complementary or identical to hybridize with their respective strands. As such, the primer sequence or probe sequence need not reflect the exact sequence of the template. Therefore, equal or more than 70%, preferably more than 80%, more preferably more than 90% and most preferably more than 95% or 99% of nucleobases on one strand of the probe or primer should be identical to the target sequence or be able to find its Watson-Crick binding partner on the other strand of the probe (or in the nucleic acid of interest) in an alignment such that the corresponding nucleotides can hybridize to each other.

As used herein, the terms "diagnostic region", "selected region" and "variable region" are interchangeable and refer to a specific region of a target polynucleotide that is suspected to have nucleotide variation(s).

As used herein, the term "hybridization" and "annealing" are interchangeable, and refers to the process by which two nucleotide sequences complementary to each other bind together to form a duplex sequence or segment.

The terms "duplex" and "double-stranded" are interchangeable, meaning a structure formed as a result of hybridization between two complementary sequences of nucleic acids. Such duplexes can be formed by the complementary binding of two DNA segments to each other, two RNA segments to each other, or of a DNA segment to an RNA segment, the latter structure being termed as a hybrid duplex. Either or both members of such duplexes can contain modified nucleotides and/or nucleotide analogues as well as nucleoside analogues. As disclosed herein, such duplexes are formed as the result of binding of one or more probes to a sample sequence.

As used herein, the terms "wild-type nucleic acid", "normal nucleic acid", "nucleic acid with normal nucleotides", "wild-type DNA" and "wild-type template" are used interchangeably and refer to a polynucleotide which has a nucleotide sequence that is considered to be normal or unaltered.

As used herein, the term "mutant polynucleotide", "mutant nucleic acid", "variant nucleic acid", and "nucleic acid with variant nucleotides", refers to a polynucleotide which has a nucleotide sequence that is different from the nucleotide sequence of the corresponding wild-type polynucleotide. The difference in the nucleotide sequence of the mutant polynucleotide as compared to the wild-type polynucleotide is referred to as the nucleotide "mutation", "variant nucleotide" or "variation." The term "variant nucleotide(s)" also refers to one or more nucleotide(s) substitution, deletion, insertion, methylation, and/or modification changes.

"Amplification" as used herein denotes the use of any amplification procedures to increase the concentration of a particular nucleic acid sequence within a mixture of nucleic acid sequences.

The term "label" and "moiety", which may be interchangeable, as used herein refers to any atom or molecule which can be used to provide or aid in the provision of, a detectable signal or not a detectable signal, which simply functions for other purposes, for example, for increasing the melting temperature of a oligonucleotide, or for resistance of nuclease degradation, or for blocking the 3' end to prevent extension, and can be attached to a nucleic acid. Labels or moieties may provide signals detectable by fluorescence, radioactivity, colorimetry, gravimetry, magnetism, enzymatic activity and the like, or may provide no signal for example dark quencher. Labels or moieties may provide no detectable signal, such as dark quencher, phosphate group etc.

The term "adjacent" or "substantially adjacent" as used herein refers to the positioning of two regions on the target nucleic acid sequence or two oligonucleotides on the complementary strand of the template nucleic acid. The two region or two oligonucleotides may be separated by 0 up to approx. 40 nucleotides, more preferably, 0, 1, 2, 3, 4, 5, 6, 7, 8, 9 or 10 nucleotides. A zero nucleotide gap means that the two regions or two oligonucleotides directly abut one another. In other words, the two regions, or the two template regions hybridised by two oligonucleotides may be contiguous, i.e. there is no gap between the two template regions. Alternatively, the two regions hybridised by the oligonucleotides may be separated by 1 to about 40 nucleotides.

The term "overlapping" as used herein refers to the positioning of two target regions, or two oligonucleotides on the complementary strand of the template nucleic acid. The two regions or the two oligonucleotides may be overlapping by 1 to about 40 nucleotides. In other words, the two regions may have a common region which is complementary to two different oligonucleotides.

The terms "labelled oligonucleotide" and "probe" are interchangeable, as used herein and refer to an oligonucleotide that is capable of forming a duplex structure by complementary base pairing with a sequence of a target polynucleotide.

The terms "thermally cycling," "thermal cycling", "thermal cycles" or "thermal cycle" refer to repeated cycles of temperature changes from a total denaturing temperature, to an annealing (or hybridising) temperature, to an extension temperature and back to the total denaturing temperature. The terms also refer to repeated cycles of a denaturing temperature and an extension temperature, where the annealing and extension temperatures are combined into one. A total denaturing temperature unwinds all double stranded fragments into single strands. An annealing temperature allows a primer to hybridize or anneal to the complementary sequence of a separated strand of a nucleic acid template. The extension temperature allows the synthesis of a nascent DNA strand of the amplicon. The term "single round of thermal cycling" means one round of denaturing temperature, annealing temperature and extension temperature. In the single round of thermal cycling, there may be internal repeats of annealing temperature and extension temperature. For example, a single round of thermal cycling may include a denaturing temperature, an annealing temperature, an extension temperature, another annealing temperature and another extension temperature. Alternatively, in a single round of thermal cycling there may be multiple annealing temperatures.

The terms "reaction mixture", "amplification mixture" or "PCR mixture" as used herein refer to a mixture of components necessary to amplify at least one amplicon from nucleic acid templates.

The mixture may comprise nucleotides (dNTPs), a thermostable polymerase, primers, and a plurality of nucleic acid templates. The mixture may further comprise a Tris buffer, a monovalent salt and $Mg^{2+}$. The concentration of each component is well known in the art and can be further optimized by an ordinary skilled artisan.

The terms "amplified product" or "amplicon" refer to a fragment of DNA amplified by a polymerase using a pair of primers in an amplification method such as PCR.

The term "melting profile" refers to a collection of measurements of an oligo (or poly)nucleotide and its complement which indicate the oligo (or poly)nucleotide molecule's transition from double-stranded to single-stranded nucleic acid (or vice-versa). The transition of a nucleic acid from double-stranded to single-stranded form is often described in the art as the "melting" of that nucleic acid molecule. The transition may also be described as the "denaturation" or "dissociation" of the nucleic acid. Accordingly, a melting profile of the present invention may also be referred to as a "dissociation profile", a "denaturation profile", a "melting curve", a "dissociation curve", a "hybridisation/dissociation profile" etc.

The practice of the present invention will employ, unless otherwise indicated, conventional techniques of molecular biology, microbiology and recombinant DNA techniques, which are within the skill of a person skilled in the art. All patents, patent applications, and publications mentioned herein, both supra and infra, are hereby incorporated by reference.

In one aspect, the invention provides a method for determining the presence or absence of variant nucleotide(s) in a diagnostic region of a target nucleic acid sequence in a sample, comprising:

(a) providing a first primer and a second primer which are capable of amplifying product comprising a sequence covering that of the diagnostic region of the target nucleic acid sequence via an amplification process, wherein the first primer comprises a sequence based on that of a first region of the target nucleic acid sequence (i.e. the first primer sequence is identical or substantially identical to the first region), wherein the first region overlaps the 5' part of the diagnostic region of the target nucleic acid sequence, but does not overlap the variant nucleotide(s), wherein the 3' end of the first region is adjacent to the 5' side of the variant nucleotide(s), in other words, the first primer is not allele-specific or mutation-specific, alternatively, the 3' end of the first region overlaps the variant nucleotide(s), wherein the first primer is allele-specific (or variant-specific, or mutant-specific) primer, which comprises 3' terminus nucleotide complementary to the variant nucleotide, wherein the second primer comprises a sequence based on that of a second region located downstream of the diagnostic region of the target nucleic acid sequence, providing a blocking oligonucleotide which can be a plain oligonucleotide without a label but with an unextendable 3' end, or preferably a labelled oligonucleotide (also referred to as a probe) comprising a detectable or undetectable moiety, the blocking oligonucleotide has a sequence based on that of the diagnostic region of a reference target nucleic acid sequence having no variant nucleotide(s) (also referred to as normal nucleotide(s)) therein, wherein the corresponding nucleotide(s) on the blocking oligonucleotide is identical to the normal nucleotide(s) on the target nucleic acid sequence, such that hybridization of the blocking oligonucleotide probe to the diagnostic region of said reference target nucleic acid sequence results in the formation of a first duplex having a first melting temperature ($T_m1$), hybridization of the blocking oligonucleotide probe to the diagnostic region of the (mutated) target nucleic acid sequence containing variant nucleotide(s) results in the formation of a second duplex having a second melting temperature ($T_m2$), wherein the $T_m2$ is lower than the $T_m1$, wherein the values of $T_m1$ and $T_m2$ are obtainable experimentally or are calculated theoretically;

(b) carrying out an amplification reaction on a reaction mixture using nucleic acid polymerase, the blocking oligonucleotide probe and the pair of first and second primers with a nucleic acid sample under conditions which are permissive for the PCR process; and (c) subjecting the amplification products to a melting analysis to determine melting temperatures of the labelled oligonucleotide probe hybridised to the PCR products, wherein the presence of a signal (or a melting peak) of the second melting temperature(s) of the second duplex in the melting profile analysis is indicative of the presence of the variant nucleotide(s) in the diagnostic region of the target nucleic acid sequence contained in the nucleic acid sample.

The PCR process can be performed normally using the build-in or normal ramping rate, or the PCR process may use slow ramping rates or multiple annealing temperatures.

The blocking oligonucleotide may be a labelled oligonucleotide probe which plays a dual role in this invention. Firstly a labelled oligonucleotide probe may act as a blocker or competitor, which binds the same area where the first primer binds. Secondly, the labelled oligonucleotide probe may act as detector, which is measured at the melting curve analysis. It should be appreciated that the labelled oligonucleotide probe may not contain any label or may contain undetectable label which may be a quencher or 3' phosphate group to block the oligonucleotide extension, which is still within the scope of the present invention. The unlabelled or undetectable probe may still act as a blocker or competitor which binds the same site as the first primer binds. The unlabelled probe or undetectable probe may not be measured at the melting curve analysis. On the other hand, the unlabelled or undetectable probe may be measured at the melting curve analysis if the reaction mixture contains double-strand binding dye, such as SYBR green.

The nucleic acid sample may be obtained from any organism, for example, viruses, bacteria, fungi, plants, and animals (including mammal and human). The nucleic acid sample can be obtained from a specimen of body fluid or tissue biopsy of a subject, or from cultured cells. The body fluid may be selected from whole blood, serum, plasma, urine, sputum, bile, stool, bone marrow, lymph, semen, breast exudate, bile, saliva, tears, bronchial washings, gastric washings, spinal fluids, synovial fluids, peritoneal fluids, pleural effusions, and amniotic fluid.

The target nucleic acid sequence may comprise a nucleic acid fragment or gene which contains variant nucleotide(s), and may be selected from the group consisting of disorder-associated SNP or gene, drug-resistance gene, and virulence gene. The disorder-associated gene may include, but is not limited to cancer-associated genes and genes associated with a hereditary disease. The cancer-associated gene may include, but is not limited to: K-ras, H-ras, N-ras, p53 (TP53), CDKN2A (p16), PIC3K, PTEN, RB1, epidermal growth factor receptor gene, BRAF, BRCA1, BRCA2, STK11, VHL, Kit and Jak2. According to this invention, the hereditary disease includes, but is not limited to, maternally inherited disorders due to mutations in mitochondrial DNA As used herein, the term "drug-resistance gene" refers to genes encoding the factors that govern the responsiveness to a drug for treatment. The drug-resistance genes may include, for example, the epithelial growth factor receptor (EGFR) gene which encodes EGFR in respect to the drug (gefitnib) for treatment of lung cancer, the multi-drug resistance-associated protein (MRP) gene encoding MRP in respect to the drug for treatment of ovarian cancer, and the lung resistance protein (LRP) gene in respect to the drug for treatment of ovarian cancer. As used herein, the term "virulence gene" refers to genes encoding virulence factors from any pathogenic organism (e.g., bacteria, protists, yeast, fungi, etc.).

The variant nucleotide(s) in the diagnostic region of the target polynucleotide sequence may include one or more nucleotide substitutions, deletions, insertions and/or abnormal methylation.

DNA methylation is an important epigenetic modification of the genome. Abnormal DNA methylation may result in silencing of tumor suppressor genes and is common in a variety of human cancer cells. In order to detect the presence of any abnormal methylation in the target polynucleotide, a preliminary treatment should be conducted prior to the practice of the present method. Preferably, the nucleic acid sample should be chemically modified by a bisulphite treatment, which will convert cytosine to uracil but not the methylated cytosine (i.e., 5-methylcytosine, which is resistant to this treatment and remains as cytosine) (R. Y. H., Wang et al. (1980), Nucleic Acids Res., 8, 4777-4790). In addition, the oligonucleotide probe should be designed based on the sequence of the bisulphite-treated wild-type DNA. With these modifications, the method of this invention can be applied to the detection of abnormal methylation(s) in the target nucleic acid.

PCR is the preferred amplification for practicing the present invention. PCR is a method for amplifying a target polynucleotide based on repeated cycles of denaturation, primer annealing and extension reaction. In fact, any amplification method involving thermal cycling is suitable. For example, a thermal cycling amplification method called polymerase chain displacement amplification (PCDR) (PCT/GB07/03793) can be used to practice the present invention.

The methods of the present invention may use normal ramping rates of temperature cycling or normal three-step or two-step cycling program. Alternatively, the methods of the present invention may use slow ramping rates or use multiple annealing temperatures. In each cycle, a reduced ramp rate including a slow cooling rate or slow heating rate may be used. The reaction may also require an increased number of cycles, for example more than 45 cycles.

During a PCR, the hybridisation (annealing) of the primer/probe to the target nucleic acid sequence in each thermal cycle may be achieved by lowering the temperature (also referred to as ramp down) slowly from a high temperature (called middle temperature, which may not be a denaturing temperature) to the lowest annealing temperature. Alternatively, the PCR may use slow heating rate to increase the temperature from an annealing temperature to an extension temperature. The PCR may also use both slow cooling rate and slow heating rate during temperature transition.

The traditional PCR is normally performed at a maximum ramp rate within each thermal cycle. In this invention, using the slow ramp rate from the middle temperature to the annealing step (or from annealing step to extension step) or using multiple annealing temperatures may increase the efficiency of amplification or may alter the sensitivity in detecting low prevalent mutations. Here an example using slow cooling rate is described. It is not necessary that the ramp down rate should be slowed directly from denaturation temperature. However it is the annealing process of the primer and probe hybridised to the target sequence that should be at a slow pace, i.e. at a slow ramp rate. It is, therefore, desirable that the temperature from the denaturation step may ramp down at a maximum rate to a temperature (herein referred to as middle temperature), at which the primer and/or probe are not annealing or are just about to anneal to the target nucleic acid sequence. From the middle temperature to the annealing temperature the ramp rate is then slowed down. The middle temperature can be the same as the first melting temperature ($T_{m1}$) of a first duplex, or preferably the middle temperature can be higher than the $T_{m1}$ by 6° C., 5° C., 4° C., 3° C., 2° C., or 1° C. Alternatively, the middle temperature can be lower than the $T_{m1}$ by 3° C., 2° C., or 1° C. The middle temperature may be in the range of the first melting temperature plus three to the first melting temperature minus two ($T_{m1}+3$ to $T_{m1}-2$). For example, if $T_{m1}=57°$ C., the middle temperature can preferably be from 60° C. to 55° C., or most preferably 57° C.

In one embodiment the PCR includes a temperature ramp-down from a denaturation temperature to the middle temperature at maximum ramp rate, and a subsequent temperature ramp-down from the middle temperature to the lowest annealing temperature at a slow ramp rate. Alternatively, PCR includes a temperature ramp-down from a denaturation temperature to the lowest annealing temperature at a maximum ramp rate, and a subsequent temperature ramp-down from the lowest annealing temperature to an extension temperature at a slow ramp rate. Alternatively, PCR includes a temperature ramp-down from a denaturation temperature to the middle temperature at maximum ramp rate, and a subsequent temperature ramp-down from the middle temperature to the lowest annealing temperature at a slow ramp rate, and a subsequent temperature ramp-down from the lowest annealing temperature to an extension temperature at a slow ramp rate. It is preferred that said slow ramp rate is lower than 2.5° C./sec, lower than 2° C./sec, lower than 1.5° C./sec, lower than 1° C./sec, or lower than 0.9° C./sec, or lower than 0.8° C./sec, or lower than 0.7° C./sec, lower than 0.6° C./sec, lower than 0.5° C./sec, lower than 0.4° C./sec, lower than 0.3° C./sec, lower than 0.2° C./sec, or lower than 0.1° C./sec. Preferred ramp rate may be between 0.5° C./sec to 0.2° C./sec or lower.

For some PCR machines, the temperature ramp rate may not be adjustable. An alternative to the above slow ramp rate is that the PCR process may include a series of multiple annealing temperatures in each cycle of the PCR thermal program, wherein said multiple annealing temperatures run in a sequence from a high annealing temperature to a low annealing temperature, or from a low annealing temperature to a higher annealing temperature within each thermal cycle. The multiple annealing temperatures may comprise at least two annealing temperatures or at least three annealing temperatures (T1, T2, T3 . . . ) or more, wherein T1 is higher than T2 which is higher than T3(T1>T2>T3), wherein in each thermal cycle, the temperatures run in a sequence from denaturing temperature, T1, T2, T3, to the extension temperature. The first annealing temperature T1 is preferably the same as the middle temperature. The second annealing temperature (T2), third annealing temperature (T3), fourth annealing temperature (T4) and so on may be proportionally spaced between the T1 and the lowest annealing temperature. Alternatively, T1 is lower than T2 which is lower than T3(T1<T2<T3), wherein in each thermal cycle, the temperatures run in a sequence from denaturing temperature, T1, T2, T3, to the extension temperature, wherein the first annealing temperature T1 is the lowest annealing temperature, the second annealing temperature (T2), third annealing temperature (T3), fourth annealing temperature (T4) and so on may be proportionally spaced between the lowest annealing temperature and the extension temperature. The lowest annealing temperature may preferably be in the range of the second melting temperature ($T_{m2}$) minus four to the second melting temperature ($T_{m2}$) plus four ($T_{m2}-4$ to $T_{m2}+4$). The lowest annealing temperature may be more preferably in the range of the second melting temperature ($T_{m2}$) minus three to the second melting temperature ($T_{m2}$) plus three ($T_{m2}-3$ to $T_{m2}+3$). The lowest annealing temperature may be more preferable in the range of the second melting temperature ($T_{m2}$) minus two to the second melting temperature ($T_{m2}$) plus two ($T_{m2}-2$ to $T_{m2}+2$). The lowest annealing temperature may be more preferable in the range of the second melting temperature ($T_{m2}$) minus one to the second melting temperature ($T_{m2}$) plus one ($T_{m2}-1$ to $T_{m2}+1$). The lowest annealing temperature may be most preferably the same as the second melting temperature ($T_{m2}$).

The thermocycling parameters are different from the traditional PCR to take advantage of the differential thermal stability of the oligonucleotide probe hybridised to the two types of target nucleic acids: the normal and mutated sequences. Assuming both the normal and mutated target sequences are present in a sample, during temperature ramp down from the middle temperature to the lowest annealing temperature, the probe strongly binds to the diagnostic region with the normal nucleotides, which is mostly paired with the probe when the temperature ramp down reaches the lowest temperature. The probe does not bind to the diagnostic region with the variant nucleotides, which is mostly paired with the first primer when the temperature ramp down reaches the lowest temperature. The first primer will have a higher chance of binding to the variant nucleic acid than binding to the normal nucleic acid. The result is that the mutated target nucleic acid is enriched in the amplification. The oligonucleotide probe in the present invention will not only play a role as the competitor (or blocker) with the amplification primer to enrich the mutated target nucleic acid, but it also plays a role as the detector. The probe may comprise detectable label, which means it can be detected. Like real-time PCR probes, the labelled oligonucleotide probe of the present invention binds to the PCR product, resulting in the signal change, which can be monitored during each cycle of the amplification. Most importantly, the probe of the present invention is used to hybridise to the PCR product at the end of the reaction for assaying the melting profile, which provides the indication as to the presence or absence of the variant nucleotides in the target sequence. In summary, firstly the labelled oligonucleotide probe of the present invention is used as a competitor (or blocker) which competes with the first primer to bind with the target nucleic acid, resulting in the enrichment of the target nucleic acid with variant nucleotide(s). Secondly, the labelled oligonucleotide probe of the present invention may be used as a real-time PCR probe, which is capable of being monitored in real-time, although this feature is not essential for the practice of the present invention. Thirdly, the labelled oligonucleotide probe of the present invention may be used for melting curve analysis at the end of PCR amplification. Lastly, an anchor probe is not needed in methods of the present invention. Many previously reported methods were using a hybridisation probe system or variant hybridisation probe system, where an anchor probe is needed (U.S. Pat. No. 7,803,543; Luo et. al. 2006, Nucleic Acid Res.; Dabritz et. al. 2005, Br. J. Cancer; Chen et. al. 2004, Clin. Chem). The reported hybridisation probe system comprises a pair of oligonucleotides—the anchor and the sensor—each labelled with a different fluorescent dye, such that fluorescence energy transfer occurs between the two when they anneal adjacent sites of a target sequence, wherein the melting curve profile of the sensor probe (designed to anneal to the variable region), allows for homogeneous genotyping in a closed tube.

In the practice of this invention, it is found that the use of a slow ramping rate or the multiple annealing temperatures may increase the amplification efficiency; it may also alter the sensitivity of mutation detection. An appropriate ramping rate or the duration and numbers of the multiple annealing temperatures in each cycle need to be chosen in consideration of the balance of the amplification efficiency and the sensitivity of mutation detection.

The PCR process in the present invention may comprise an extension reaction set to run at a temperature higher than the first melting temperature of the first duplex. It should be appreciated that without this extension reaction the method still works, although it may not be optimal. It is well known that during the annealing step, the annealed primer may be extended because the DNA polymerase used in the PCR process can extend the primer at various temperatures, which can be below the optimal temperatures.

The duration time at each step, including the denaturation, multiple annealing and extension, can be determined normally as with the standard PCR. The duration time may be important for methods of this invention, as the length at each annealing temperature may affect the sensitivity or efficiency of amplification and detection of rare mutations.

In one embodiment the first primer hybridises (anneals) to a region in the target nucleic acid sequence, so that PCR amplification can take place. This region in the target nucleic acid sequence is referred to as the first region. The target nucleic acid is normally double-stranded; the first region referred to herein means both strands of the same region in the double-stranded target nucleic acid. The first primer is complementary or substantially complementary to one strand of the first region; at the same time, it is also true that the first primer is identical or substantially identical to the opposite strand of the first region.

The blocking oligonucleotide hybridises to a diagnostic region in the target nucleic acid sequence. The diagnostic region is a region where variant nucleotide(s) may be present. The diagnostic region referred to herein means both strands of the same region in the double-stranded target nucleic acid, where the variant nucleotide(s) are located. The blocking oligonucleotide probe is complementary or substantially complementary to one strand of the diagnostic region; at the same time, it is also true that the blocking oligonucleotide probe is identical or substantially identical to the opposite strand of the diagnostic region.

To simplify the explanation, hereinafter the first region and the diagnostic region of the target sequence are referred to as one of the strands in the first region and the diagnostic region, respectively, having the same or similar sequence to the first primer and the blocking oligonucleotide probe.

Numbering provided with reference to the figures is provided to assist in understanding and should not be construed as limiting.

In one embodiment, the first region (26) overlaps the 5' part of the diagnostic region (12) of the target nucleic acid sequence (14), but does not overlap the variant nucleotide(s) (10). The 3' end of the first region is adjacent to the 5' side of the variant nucleotide(s) (FIG. 1). The first primer (16) anneals to the first region, some of which is also part of the diagnostic region, but it does not anneal to the variant nucleotide(s). In other words, the first primer is not allele-specific or mutation-specific.

In another embodiment, the 3' end of the first region overlaps the variant nucleotide(s), wherein the first primer is allele-specific (or variant-specific, or mutant-specific) primer, which comprises 3' terminus nucleotide complementary to the variant nucleotide.

In one embodiment, the 3' end of the first region may abut the 5' side of at least one of the variant nucleotide(s) in the diagnostic region of the target nucleic acid sequence, wherein the annealed first primer is extended, the first extended nucleotide is the variant nucleotide. The first primer anneals to the first region with the 3' end immediately next to the variant nucleotide.

In another embodiment, the 3' end of the first region may be spaced apart from the 5' of the variant nucleotide(s) by one to nine nucleotides, wherein when the annealed first primer is extended, the second to tenth extended nucleotide(s) are the variant nucleotide(s). In other words, the first primer anneals to the first region one to nine nucleotides away from the variant nucleotide(s).

The diagnostic region may be divided into two parts: the 5' part and 3' part, or may comprise an additional unmatched part which is located between the 5' part and 3' part. The 5' part of the diagnostic region matches or is similar to the 5' portion of the probe (20). The 3' part of the diagnostic region matches or is similar to the 3' portion of the probe. The unmatched part of the diagnostic region does not have matching sequence to the probe. The 5' part of the diagnostic region overlaps with the first region. In other words, the 5' part of the diagnostic region and the first region comprise some common sequence. It should be appreciated that the 5' part of the diagnostic region and the first region may comprise other sequence that is not common. The 3' part of the diagnostic region contains variant nucleotide(s). The diagnostic region may contain a single mutation, for example BRAF V600E, or may contain potential multiple mutation sites, for example mutations in Kras codon 12 and codon 13.

The length of the first region and the diagnostic region are dependent on the sizes of the first primer (16) and the oligonucleotide probe (20).

It is preferred that the first primer, capable of hybridising to the target nucleic acid sequence, has a melting temperature which is in the range of the second melting temperature ($T_{m2}$) minus five to the second melting temperature ($T_{m2}$) plus five ($T_{m2}-5$ to $T_{m2}+5$). It is more preferred that the first primer, capable of hybridising to the target nucleic acid sequence, has a melting temperature which is in the range of the second melting temperature ($T_{m2}$) minus three to the second melting temperature ($T_{m2}$) plus three ($T_{m2}-3$ to $T_{m2}+3$). It is even more preferred that the first primer, capable of hybridising to the target nucleic acid sequence, has a melting temperature which is the same or similar as the second melting temperature or lower than the second melting temperature by 1° C. to 5° C.

The first primer (16) and second primer (18) preferably comprise naturally occurring nucleotides, although modified nucleotides or linkages can be included in the first and second primer.

In one embodiment, the blocking oligonucleotide may comprise naturally occurring nucleotides only. In other embodiments the blocking oligonucleotide may comprise naturally occurring nucleotides and modified nucleotides or linkages. It may not be desirable that the blocking oligonucleotide probe is solely made of PNA or LNA. The modified nucleotides or linkages may comprise LNA, PNA, d(2-am)ATP, 5-methylcytosine, minor groove binders, phosphorothioate linkages, superbase or base analogues. Sometimes the blocking oligonucleotide probe comprises one or more modified nucleotides or bases. The nucleotide(s) corresponding to the variant nucleotides may be modified.

The blocking oligonucleotide probe may comprise nucleotides, nucleotide derivatives, nucleotide analogs, and/or non-nucleotide chemical moieties. Modifications of the probe that may facilitate or enhance probe binding include, but are not limited to, the incorporation of minor groove binders; the incorporation of positively charged or neutral phosphodiester linkages in the probe to decrease the repulsion of the polyanionic backbones of the probe and target (see Letsinger et al., 1988, J. Amer. Chem. Soc. 110:4470); the incorporation of alkylated or halogenated bases, such as 5-bromouridine, in the probe to increase base stacking; the incorporation of ribonucleotides into the probe to force the probe:target duplex into an "A" structure, which has increased base stacking; the substitution of 2,6-diaminopurine (amino adenosine) for some or all of the adenosines in the probe, and/or the substitution of 5-methylcytosine for cytosine in the probe; the incorporation of nucleotide derivatives such as LNA (locked nucleic acid), PNA (peptide nucleic acid) or the like.

It is preferred that a moiety that enhances the binding of the blocking oligonucleotide probe to the target sequence is attached to the 3' part of the probe, or at the 3' end of the probe, or at the 5' end of the probe. For example, a minor groove binder may be attached at the 3' end or 5' end of the probe, fluorophore and/or quencher may be attached at the 3' end or 5' end of the probe. Some nucleotide analogs that increase the binding of the probe to the target sequence may be positioned at any nucleotides or preferably positioned at the nucleotides surrounding or corresponding to the variant nucleotides. Alternatively, the probe may be just a plain oligonucleotide with the 3' end blocked.

Generally the 3' terminus of the blocking oligonucleotide probe will be "blocked" or made "unextendable" to prohibit incorporation of the probe into a primer extension product. The probe can be made unextendable by using non-complementary bases or by adding a chemical moiety such as dye, a quencher, biotin or a phosphate group to the 3' hydroxyl of the last nucleotide, which may, depending upon the selected moiety, serve a dual purpose by also acting as a label for subsequent detection or capture of the nucleic acid attached to the label. The probe can also be made unextendable by removing the 3'-OH or by using a nucleotide that lacks a 3'-OH such as a dideoxynucleotide.

The blocking oligonucleotide probe comprises detectable or undetectable moiety (label) which may include, but not limited to, a fluorescent moiety, a photoluminescent moiety, a luminescent moiety, quencher moiety, minor groove binder moiety or a chemiluminescent moiety.

In a preferred embodiment of the present invention, when the first primer is not an allele-specific primer, the PCR process in the method uses high fidelity (proof reading) DNA polymerase, which possesses 3' to 5' exonuclease activity. The blocking oligonucleotide is modified at the 3' part such that the blocking oligonucleotide is not digested by the 3' to 5' exonuclease activity of the high fidelity DNA polymerase. The blocking oligonucleotide may be modified by phosphorothioate linkages at the 3 part.

When the blocking oligonucleotide probe comprises detectable label (F), the signal intensity of the probe is either increased or decreased by hybridization. The probe may be labelled by a single detectable moiety (FIG. 3C, D) or may be labelled by multiple moieties (F; Q) (FIG. 3 A).

The label on the probe may be a fluorophore (F) or a quencher (Q) (a non-fluorescent dye). In one embodiment, the labelled oligonucleotide contains a single label, which is attached to the 5' or 3' end of the oligonucleotide (FIG. 3B, C, E, F). Alternatively, the probe may comprise an interactive pair of labels, for example fluorophores and/or non-fluorophore dyes (FIG. 3A). One example of such interactive labels is a fluorophore-quencher pair. The label on the probe can be located anywhere, as long as it interacts with other labels or other entities such as G nucleotides on the oligonucleotide.

The labelled oligonucleotide probe may comprise a reporter label and a quencher label, wherein the quencher label is capable of quenching the fluorescence of said reporter label when said oligonucleotide probe is in a single-stranded conformation and is not hybridized to said target nucleic acid, wherein said oligonucleotide probe is capable of forming a double stranded conformation when hybridized to said target nucleic acid, where the fluorescence of said reporter label is unquenched such that the fluorescence intensity of said reporter label is greater than the fluorescence intensity of said reporter label when said oligonucleotide probe is in a single stranded conformation not hybridized to said target nucleic acid.

In one embodiment, labels are attached at both ends of the probe, for example, a fluorophore is attached to the 5' end of the probe and a quencher is attached to the 3' end of the probe.

In another embodiment, a quencher label is attached at 3' end of the probe and a reporter label is attached to an internal nucleotide of the probe. This design is especially useful for a long probe with more than 25 nucleotides. The internal reporter label is generally less than 20 nucleotides away from 3' end, or preferably less than 19 nucleotides away from 3' end, or more preferably less than 18 nucleotides away from 3' end, or more preferably less than 17 nucleotides away from 3' end, or more preferably less than 16 nucleotides away from 3' end, or more preferably less than 15 nucleotides away from 3' end, or more preferably less than 14 nucleotides away from 3' end, or more preferably less than 13 nucleotides away from 3' end, or more preferably less than 12 nucleotides away from 3' end, or more preferably less than 11 nucleotides away from 3' end, or more preferably less than 10 nucleotides away from 3' end. The internal reporter label may be less than 9 nucleotides away from 3' end, or less than 8 nucleotides away from 3' end, or less than 7 nucleotides away from 3' end, or less than 6 nucleotides away from 3' end, or less than 5 nucleotides away from 3' end (FIG. 1). This type of probe is not suitable for hydrolysis probe-based real-time PCR, but is designed for signal generation by hybridisation with amplified product and melting curve analysis of probe-amplicon duplex.

The quencher label is preferably a non-fluorescent dye label, which may be attached to the 3' terminus or 5' terminus of the oligonucleotide probe, or to an internal residue of the oligonucleotide probe. The reporter label may be a fluorescent dye label, which may be attached to an internal residue of the oligonucleotide probe, or to the 5' terminus or 3' terminus of the oligonucleotide probe. The reporter label is preferably a fluorophore, which may be selected from the group consisting of fluorescein, fluorescein derivatives, cyanine dyes, fluorescein-cyanine conjugates, and similar.

"Fluorophore" is used herein to refer to a moiety that absorbs light energy at a defined excitation wavelength and emits light energy at a different defined wavelength. Examples of fluorescence labels include, but are not limited to: Alexa Fluor dyes (including Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethyl-rhodamine (TAMRA), Texas Red and Texas Red-X.

As used herein, the term "quencher" includes any moiety that is capable of absorbing the energy of an excited fluorescent label when it is located in close proximity to the fluorescent label and capable of dissipating that energy. A quencher can be a fluorescent quencher or a non-fluorescent quencher, which is also referred to as a dark quencher. The fluorophores listed above can play a quencher role if brought into proximity to another fluorophore, wherein either FRET quenching or contact quenching can occur. It is preferred that a dark quencher which does not emit any visible light is used. Examples of dark quenchers include, but are not limited to, DABCYL (4-(4'-dimethylaminophenylazo) benzoic acid) succinimidyl ester, diarylrhodamine carboxylic acid, succinimidyl ester (QSY-7), and 4',5'-dinitrofluorescein carboxylic acid, succinirnidyl ester (QSY-33), quencherl, or "Black hole quenchers" (BHQ-1, BHQ-2 and BHQ-3), nucleotide analogs, nucleotide G residues, nanoparticles, and gold particles.

Since the diagnostic region may be divided into: the 5' part, 3' part and optional unmatched part, the blocking oligonucleotide may also be divided into two portions, a first portion comprising sequence substantially identical to the 5' part sequence of the diagnostic region, and a second portion comprising sequence substantially identical to the 3' part sequence of the diagnostic region, wherein the first portion and second portion of the blocking oligonucleotide probe are contiguous, the 5' part and 3' part of the diagnostic region may be contiguous or may not be contiguous. In one embodiment, the blocking oligonucleotide probe has a sequence identical to the diagnostic region of the target sequence. Alternatively, the diagnostic region of the target sequence may comprise some sequence (the unmatched part) that is not present in the blocking oligonucleotide probe. In other words, the blocking oligonucleotide comprises non-match extra nucleotides or nucleotide deletions in the middle positions of the blocking oligonucleotide. The non-match extra nucleotides or nucleotide deletions can be one, two, three or more than three nucleotides, which can be located at the middle of the blocking oligonucleotide or scattered at different locations of the blocking oligonucleotide. Nucleotide deletions are preferred. The nucleotide deletions or the extra nucleotides reduce the Tm of the blocking oligonucleotide and play a role to widen the difference between Tm1 and Tm2. The nucleotide deletions or the extra nucleotides also allow the blocking oligonucleotide to block the primer binding on the wild-type sequence more efficiently, as the overlapping part between the first region and the diagnostic region can be large. In some applications, it is preferred that the blocking oligonucleotide probe hybridises to the diagnostic region with mismatch nucleotides or bulge, which are preferably located between the 5' part and 3' part of the diagnostic region.

The blocking oligonucleotide probe used in the present invention is not degradable, even when the reaction mix comprises DNA polymerase with 5' nuclease activity or with 3' to 5' exonuclease activity. The blocking oligonucleotide probe, the first primer and the amplified PCR product are not able to form a structure recognizable by the 5' nuclease activity of a DNA polymerase. The blocking oligonucleotide probe may be modified at 3' part such that it cannot be cleaved by the 3' to 5' exonuclease activity of a DNA polymerase.

In the above mentioned methods, the blocking labelled oligonucleotide and second primer are separate molecules, i.e. they are not linked. The inventor has found that the method of the present invention can work equally well when the labelled oligonucleotide (20) and second primer (18) are linked together, i.e. they are linked to become a single oligonucleotide (18'-20'). The labelled oligonucleotide probe is attached at 5' end of the second primer (FIG. 2). This oligonucleotide is named as linked-primer-probe (18'-20'), which comprises a 5' probe portion and a 3' primer portion. The probe portion in the linked-primer-probe may have all or most characteristics similar to the labelled oligonucleotide probe described above. However, the linkage of second primer and probe makes this new molecule having some novel properties. This linked-primer-probe acts as primer and initiates extension on the template. Upon denaturation the extended strand is separated from the template. Under hybridisation condition, the probe portion in the linked-primer-probe on the extended strand folds back and hybridise with its extended strand, creating a stem-loop structure (32) (FIG. 2). In this stem-loop structure, the probe portion in the linked second primer-probe plays the same role as labelled oligonucleotide probe in the methods described above, where probe and second primer are separate molecules.

The 5' probe portion in the linked-primer-probe is mismatched to the mutated target sequence, destabilizing the stem-loop structure and allowing the primer to hybridise to the stem part of the secondary structure and complete the extension of the full-length PCR product. The probe portion in the linked-primer-probe is matched to the wild-type target sequence, blocking primer hybridisation with the stem part of the secondary structure and limiting formation of the full-length PCR product (FIG. 2). A 1 or 2-bp mismatch at the 5' end probe portion of the linked-primer-probe may be included to prevent 3'-end extension of the stem-loop of the first primer extended strand that may form from the full-length single strand. The 5' probe portion and 3' primer portion may be linked by normal nucleotide(s), so that polymerase can copy the whole linked primer-probe. Alternatively, the 5' probe portion and 3' primer portion may be linked by a chemical moiety which can't be copied, such as a hydrocarbon arm, an HEG, non-nucleotide linkage, a basic ribose, nucleotide derivatives or a dye, so that polymerase cannot copy a part or the whole probe portion of the linked primer-probe. One of the labels may be attached to the chemical moiety which can't be copied, such as a basic ribose.

Since the first primer and blocking oligonucleotide comprise some common sequence, they compete in binding to the same area of the target nucleic acid sequence. When a variant nucleotide(s) is present, the probe does not bind strongly, therefore, the first primer has a higher chance of binding and extending, resulting in preferential amplification of the target nucleic acid containing the variant nucleotide(s). The melting profile reveals that a melting peak with a temperature the same as or similar to the second melting temperature is present.

When the first primer is not an allele-specific primer, and when the variant nucleotide(s) is not present, the first primer may still bind to the target nucleic acid sequence containing the normal nucleotide(s) and extend, resulting in the generation of the PCR product of the normal target nucleic acid, which could serves as a PCR control.

In the method of the present invention, when the first primer is not an allele-specific primer and if both normal and variant nucleotides are present in the target nucleic acid sequence, depending on the ratio of variant and normal target nucleic acids, both melting peaks of $T_{m1}$ and $T_{m2}$ may be visible in the melting profile analysis at the end of the PCR. When the variant nucleic acid is present at a high proportion, the melting profile may only show the melting peak with $T_{m2}$. When the variant nucleic acid is present at a certain proportion, the melting profile may show both the melting peaks with $T_{m1}$ and $T_{m2}$, the relative height of both peaks will give an indication as to the amount of each target nucleic acid in comparison with standard controls with known concentrations of each target. When the sample contains the normal nucleic acid only, the melting profile will only show the melting peak with $T_{m1}$, which gives an indication that the PCR works and there is no variant nucleic acid present in the sample. Although the present method is largely a detection of presence or absence, it can also provide some quantitative data. As mentioned above, the relative melting peak heights of $T_{m1}$ and $T_{m2}$ give an indication of the amount of each target nucleic acid present. Compared with a standard control with known concentrations, the quantitative data can be precise.

The variant nucleotide(s) may include one or more nucleotide substitutions, deletions, insertions, or abnormal methylation.

The amplification reaction used in the present invention is preferably PCR, although other amplification methods can be used. One important factor affecting the sensitivity of detecting mutations which are present at a low frequency in a sample is the concentration ratio between the first primer and the blocking oligonucleotide probe. Generally, the concentration ratio of first primer/labelled oligonucleotide probe is less than one. However, one cannot determine precisely which ratio would work best, unless various ratios are tried in experiments. In fact, the measured concentration of an oligonucleotide from the manufacturer is not always accurate. Any subtle inaccuracy will affect the ratio of the two oligonucleotides, so one has to do an experiment to check that a correct amount of primer and probe are applied. The trend is that the lower the ratio, the higher the sensitivity. However, if the ratio is too low, which means too little first primer is used, the PCR may not work effectively.

When the first primer is not an allele-specific primer, asymmetric PCR may be typically performed with an excess of the second primer. Any DNA polymerase can be used. For detecting a low concentration of mutant sequences in a background of normal sequences, a proof reading (or high fidelity) DNA polymerase with the 3' to 5' exonuclease may be used, for example, PWO DNA polymerase, Pfu DNA polymerase, Vent DNA polymerase, or KOD DNA polymerase. The non-proof reading DNA polymerase may introduce PCR errors into the PCR product, which may interfere with the true mutation. The proof reading DNA polymerase has a lower error rate, and helps detecting rare mutated DNA in a sample, especially the formalin-fixed paraffin-embedded (FFPE) sample.

The present invention also provides a method of analysing a biological sample for the presence and/or the amount of mutations or polymorphisms at multiple loci of different target nucleic acid sequences in a single reaction vessel. For example, detecting Kras codons 12-13 and BRAF V600E can be done in a single reaction, detecting EGFR mutations exon 21 L858R, exon 19 deletions and exon 20 mutation T790M can also be done in a single reaction. The primers and probes for Kras and BRAF can be mixed together in a single PCR reaction. The probes for Kras and BRAF may be labelled by different dyes so that they can be detected in different detection channels.

The amplification reaction mixture will comprise standard amplification reagents. A sample is provided which is suspected to contain the target nucleic acid or the nucleotide variant of interest. The target nucleic acid contained in the sample may be double-stranded genomic DNA or cDNA if necessary, which is then denatured, using any suitable denaturing method. The denatured nucleic acid strands are then incubated with oligonucleotide primers and probes under hybridisation conditions, i.e. conditions that enable the binding of the primers and/or probes to the single nucleic acid strands.

In another aspect, the present invention provides a method for determining the presence or absence of variant nucleotide(s) in a diagnostic region of a target nucleic acid sequence in a sample, comprising:

(a) providing a first primer and a second primer which are capable of amplifying a product comprising a sequence covering that of the diagnostic region of the target nucleic acid sequence via an amplification process, wherein the first primer comprises a sequence based on that of a first region of the target nucleic acid sequence (i.e. the first primer sequence is identical or substantially identical to the first region), the first region overlaps the 5' part of the diagnostic region of the target nucleic acid sequence, and the 3' end of the first region overlaps the variant nucleotide(s), and in which the first primer is an allele-specific (or variant-specific) primer, which comprises a 3' terminus nucleotide complementary to the variant nucleotide, and the second primer comprises a sequence based on that of a second region located downstream of the diagnostic region of the target nucleic acid sequence, providing a blocking oligonucleotide probe which may be a plain oligonucleotide without detectable label but with an unextendable 3' end, or a labelled oligonucleotide probe comprising a moiety, and in which the blocking oligonucleotide probe has a sequence based on that of the diagnostic region of a reference target nucleic acid sequence having no variant nucleotide(s) (also referred to as normal nucleotide(s)) therein, wherein the corresponding nucleotide(s) on the blocking oligonucleotide probe is identical to the normal nucleotide(s) on the target nucleic acid sequence, such that hybridization of the blocking oligonucleotide probe to the diagnostic region of said reference target nucleic acid sequence results in the formation of a first duplex having a first melting temperature ($T_m1$), hybridization of the blocking oligonucleotide probe to the diagnostic region of the (mutated) target nucleic acid sequence containing variant nucleotide(s) results in the formation of a second duplex having a second melting temperature ($T_m2$), wherein the $T_m2$ is lower than the $T_m1$, wherein the values of $T_m1$ and $T_m2$ are obtainable experimentally or are calculated theoretically, wherein the blocking oligonucleotide probe comprises non-match extra nucleotides or nucleotide deletions in the middle positions of the blocking oligonucleotide probe, wherein when the blocking oligonucleotide probe hybridises to the diagnostic region of a nucleic acid target, the hybridisation creates an unpaired base bulge, which is either located on the blocking oligonucleotide probe (in case of the extra unmatched nucleotides in the blocking oligonucleotide probe) or on the template (in case of the nucleotide deletions in the blocking oligonucleotide probe), optionally providing a detector probe which is capable of hybridising to the amplified target sequence (FIG. 3B), (b) carrying out an amplification reaction on a reaction mixture using nucleic acid polymerase, the blocking oligonucleotide probe, optionally a detector probe and the pair of the first and second primers with a nucleic acid sample under conditions which are permissive for the amplification process; and (c) if the first primer comprises label(s), detecting the amplified products by a melting profile analysis of the amplicons, or if the reaction comprises a detector probe, detecting the amplified product by detecting a change in the detectable signal of the detector probe.

The detector probe may be an ordinary real-time PCR probe, which can be TaqMan probe, Molecular beacon or hybridisation probe.

In another aspect, the present invention provides a method for determining the presence or absence of variant nucleotide(s) in a diagnostic region of a target nucleic acid sequence in a sample, comprising:

(a) providing a first primer and a second primer which are capable of amplifying a product comprising a sequence covering that of the diagnostic region of the target nucleic acid sequence via an amplification process, wherein the first primer comprises a sequence based on that of a first region of the target nucleic acid sequence (i.e. the first primer sequence is identical or substantially identical to the first region), the first region overlaps the 5' part of the diagnostic region of the target nucleic acid sequence, and the 3' end of the first region overlaps the variant nucleotide(s), and in which the first primer is an allele-specific (or variant-specific) primer, which comprises a 3' terminus nucleotide complementary to the variant nucleotide, and the second primer comprises a sequence based on that of a second region located downstream of the diagnostic region of the target nucleic acid sequence, providing a blocking oligonucleotide probe which may be a plain oligonucleotide without a detectable label but with an unextendable 3' end, or a labelled oligonucleotide probe comprising a moiety, and in which the blocking oligonucleotide probe has a sequence based on that of the diagnostic region of a reference target nucleic acid sequence having no variant nucleotide(s) (also referred to as normal nucleotide(s)) therein, wherein the corresponding nucleotide(s) on the blocking oligonucleotide probe is identical to the normal nucleotide(s) on the target nucleic acid sequence, such that hybridization of the blocking oligonucleotide probe to the diagnostic region of said reference target nucleic acid sequence results in the formation of a first duplex having a first melting temperature ($T_m1$), hybridization of the blocking oligonucleotide probe to the diagnostic region of the (mutated) target nucleic acid sequence containing variant nucleotide(s) results in the formation of a second duplex having a second melting temperature ($T_m2$), wherein the $T_m2$ is lower than the $T_m1$, wherein the values of $T_m1$ and $T_m2$ are obtainable experimentally or are calculated theoretically, wherein the moiety on the labelled oligonucleotide probe may be attached to the 3' end and/or the 5' end, and is capable of increasing the melting temperature of the labelled oligonucleotide probe in comparison to the plain oligonucleotide without the moiety, wherein the moiety may be a fluorescent dye or a non-fluorescent dye, which may be a fluorophore or a quencher, optionally providing a detector probe which is capable of hybridising to the amplified target sequence (FIG. 3B), (b) carrying out an amplification reaction on a reaction mixture using nucleic acid polymerase, the blocking oligonucleotide probe, optionally a detector probe and the pair of the first and second primers with a nucleic acid sample under conditions which are permissive for the amplification process; and (c) if the first primer comprises label(s), detecting the amplified products by a melting profile analysis of the amplicons, or if the reaction comprises a detector probe, detecting the amplifed product by detecting a change in the detectable signal of the detector probe.

The detector probe may be an ordinary real-time PCR probe, which can be TaqMan probe, Molecular beacon or hybridisation probe.

In another aspect, the present invention provides a method for determining the presence or absence of variant nucleotide(s) in a diagnostic region of a target nucleic acid sequence in a sample, comprising:

(a) providing a first primer and a second primer which are capable of amplifying a product comprising a sequence covering that of the diagnostic region of the target nucleic acid sequence via an amplification process, wherein the first primer comprises a sequence based on that of a first region of the target nucleic acid sequence (i.e. the first primer sequence is identical or substantially identical to the first region), the first region overlaps the 5' part of the diagnostic region of the target nucleic acid sequence, and the 3' end of the first region overlaps the variant nucleotide(s), and in which the first primer is an allele-specific (or variant-specific) primer, which comprises a 3' terminus nucleotide complementary to the variant nucleotide, and the second primer comprises a sequence based on that of a second region located downstream of the diagnostic region of the target nucleic acid sequence, wherein the allele-specific primer comprises one, two, three or more than three non-match extra nucleotides, alternatively one, two, three, more than three nucleotide deletions in the positions within ten, nine, eight, seven, six, five, four or three nucleotides from the 3' terminus of the primer, wherein when this type of primer anneals to the primer binding site of a nucleic acid target, the hybridisation creates an unpaired base bulge, which is either located on primer (in the case of the extra unmatched nucleotides in the primer) or on the template (in the case of the nucleotide deletions in the primer), and/or providing an oligonucleotide probe which acts as a blocker having a sequence based on that of the diagnostic region of a reference target nucleic acid sequence having no variant nucleotide(s) therein, where the oligonucleotide probe comprises non-match extra nucleotides or nucleotide deletions in middle positions of the oligonucleotide probe, such that when the oligonucleotide probe hybridises to the diagnostic region of a nucleic acid target hybridisation creates an unpaired base bulge, which is either located on the oligonucleotide probe in the case of the extra unmatched nucleotides in the oligonucleotide probe or on the template in the case of the nucleotide deletions in the oligonucleotide probe, optionally providing a detector probe which is capable of hybridising to the amplified target sequence (FIG. 3B), (b) carrying out an amplification reaction on a reaction mixture using nucleic acid polymerase, the blocking oligonucleotide probe, optionally a detector probe and the pair of the first and second primers with a nucleic acid sample under conditions which are permissive for the amplification process; and (c) if the first primer comprises label(s), detecting the amplified products by a melting profile analysis of the amplicons, or if the reaction comprises a detector probe, detecting the amplified product by detecting a change in the detectable signal of the detector probe.

The detector probe may be an ordinary real-time PCR probe, which can be TaqMan probe, Molecular beacon or hybridisation probe.

The blocking oligonucleotide probe plays a role as blocker, which competes with first primer in binding to the same or a similar site of a target region. The blocking oligonucleotide probe comprises non-match extra nucleotides or nucleotide deletions in the middle positions of the blocking oligonucleotide, the non-match extra nucleotides or nucleotide deletions can be one, two, three or more than three nucleotides, which can be located at the middle of the blocking oligonucleotide or scattered at different locations of the blocking oligonucleotide. Nucleotide deletions are preferred. The nucleotide deletions or the extra nucleotides reduce the Tm of the blocking oligonucleotide and play a role to widen the difference between Tm1 and Tm2. The nucleotide deletions or the extra nucleotides also enable the blocking oligonucleotide to block the primer binding on the wild-type sequence more efficiently, as the overlapping part between the first region and the diagnostic region can be large. The blocking oligonucleotide can be a labelled oligonucleotide probe. The moiety on the labelled oligonucleotide may be attached to the 3' end and/or the 5' end, and is capable of increasing the melting temperature of the labelled oligonucleotide in comparison with the plain oligonucleotide without the moiety, wherein the moiety may be a fluorescent dye or non-fluorescent dye, which can be a fluorophore or a quencher.

When the first primer is an allele-specific primer, the first primer may comprises one, two, three or more than three non-match extra nucleotides, alternatively one, two, three, or more than three nucleotide deletions in the positions within six, five, four or three nucleotides from the 3' terminus of the primer, wherein when this type of primer anneals to the primer binding site of a nucleic acid target in a sample, the hybridisation creates an unpaired base bulge, which is either located on the primer (in case of the extra unmatched nucleotides in the primer) or on the template (in the case of the nucleotide deletions in the primer), wherein the 3'-terminal base of the first primer is complementary to the variant base being detected. The amplification reaction may comprise the use of a plurality of first primers for multiplex detection of multiple variant nucleotides. The first primer may not comprise a label. Alternatively, different first primers may comprise different labels or the same label in different sequence contexts, where the label may increase or decrease the detection signal when the first primers are incorporated into the amplified products.

The first primer may be attached with a fluorophore at the 5' end and with a quencher at an internal nucleotide, alternatively the first primer may be attached with a quencher at the 5' end and with a fluorophore at an internal nucleotide or the first primer may be attached with a fluorophore at the 5' end and with a same or a different fluorophore at an internal nucleotide (FIG. 3F), such that when the primer is incorporated into the amplified product, the fluorescent signal is increased, and the amplified product is capable of being analysed by melting curve analysis. The distance between the labels (fluorophore or quencher) at the 5' end and at the internal nucleotide, may be more than 4 nucleotides but less than 25 nucleotides, or may be more than 5 nucleotides but less than 20 nucleotides, or may be more than 6 nucleotides but less than 15 nucleotides.

The allele-specific first primer may be designed with a mismatch in the position of the second nucleotide from the 3' terminus nucleotide, or the third nucleotide from the 3' terminus nucleotide or the fourth nucleotide from the 3' terminus nucleotide with respect to both the mutant and wild-type alleles. The second nucleotide from the 3' terminus nucleotide of the allele-specific primer is popularly termed as 3'-penultimate nucleotide position. The 3'-terminal base of the first primer is complementary to the variant base being detected. This design results in a single 3'-terminal mismatch between the mutant-specific primer and the wild-type template, but a double, 3'-terminal mismatch between the mutant-specific primer and the wild-type template. It has been shown that greater allele selectivity is achieved by this design.

In another embodiment, the allele-specific first primer may be designed with one, two, three or more than three non-match extra nucleotides, alternatively one, two, three or more than three nucleotide deletions in the positions within ten, nine, eight, seven, six, five, four or three nucleotides from the 3' terminus. When this type of primer anneals to the primer binding site of a nucleic acid target in a sample, the hybridisation creates a bulge, which is either located on the primer (in the case where there are extra unmatched nucleotides in the primer) or on the template (in the case where there are nucleotide deletions in the primer). The 3'-terminal base of the first primer is complementary to the variant base being detected. This design results in an unmatched base bulge on the unmatched nucleotide positions but complementary 3' ends between the mutant-specific primer and the mutant template, which may cause efficient primer extension. However a double, or triple or more 3'-end mismatches between the mutant-specific primer and the wild-type template may inhibit primer extension. It has been shown that greater allele selectivity is achieved by this design. Examples of such design were demonstrated in detecting EGFR exon 21 mutations L858R and L861Q (Example 4).

The mutation-specific primer for L858R has a sequence:

```
                                            SEQ ID NO. 21
        5'-CAAGATCACAGATTTTGGCG-3'
``` which was designed to have a nucleotide "G" deletion within five nucleotides from the 3' end.

The mutation-specific primer for L861QR has a sequence:

```
                                            SEQ ID NO. 22
        5'-GATTTTGGGCTGGCCAACA-3'
``` which was designed to have a nucleotide "A" deletion within five nucleotides from the 3' end.

For detecting EGFR exon 20 T790M mutation, the mutation-specific primer for T790M has a sequence:

```
                                            SEQ ID NO. 24
        5'-CCGAAGGGCATGAGCTCA-3'
``` which was designed to have a nucleotide "G" deletion within three nucleotides from the 3' end.

The present invention also provides a method and primers for detecting EGFR exon 21 mutations L858R and L861Q and exon 20 mutation T790M.

The primer does not need to be the exact length same as these primers, as long as they can be used in an amplification reaction under appropriate conditions. Any primer comprising a 3' part sequence identical to the sequence of the 3' part of any of these three primers is within the scope of this invention. The 3' part of any of these three primers can be 18 nucleotides from the 3' end, or 17 nucleotides from the 3' end, or 16 nucleotides from the 3' end, or 15 nucleotides from the 3' end, or 14 nucleotides from the 3' end, or 13 nucleotides from the 3' end, or 12 nucleotides from the 3' end, or 11 nucleotides from the 3' end, or 10 nucleotides from the 3' end, or 9 nucleotides from the 3' end, or 8 nucleotides from the 3' end.

The labelled oligonucleotide may comprise a detectable or undetectable label, functioning as a blocker of wild-type amplification. It has been found that the label on the probe can increase the melting temperature of an oligonucleotide, such that 5' or 3' end labelled fluorophores or quenchers can increase oligonucleotide's Tm by 2° C. to 6° C. The label must be attached at the terminus, either at the 5' or 3' end, or both ends of an oligonucleotide (FIG. 3B, C, E, F).

It was also found that the first primer can comprise label(s), which can be used for monitoring PCR amplification and for melting curve analysis. Depending on which nucleotide the label is attached to, the signal can increase or decrease when the primer is incorporated into a PCR product. A very useful design is that the primer is attached with a fluorophore or quencher at the 5' end and at an internal nucleotide (FIG. 3F). The combinations can be 5' fluorophore-internal fluorophore, 5' fluorophore-internal quencher or 5' quencher-internal fluorophore.

The reaction may contain detector probe which is labelled and first primers which are not labelled. The reaction may comprise both a labelled first primer and a detector probe. In the step (c), detecting the amplified products may be achieved by a melting profile analysis of the amplicons and by detecting a change in the detectable signal of the detector probe.

In another aspect, the present invention provides a labeled oligonucleotide primer (first primer) for assaying a target nucleic acid sequence in a sample, comprising: a reporter label and a quencher label (or another reporter label), wherein said oligonucleotide primer is capable of forming a double stranded conformation when hybridized to the target nucleic acid or incorporated into a primer extension product, where the fluorescence of said reporter label is unquenched, wherein said quencher label is a non-fluorescent label, which is attached to an internal nucleotide of the oligonucleotide primer or to the 5' end of the primer, wherein said reporter label is a fluorescent dye label (or a fluorophore), which is attached to the 5' end of the oligonucleotide primer or to an internal nucleotide, alternatively, the labeled oligonucleotide primer comprises two reporter labels, one of which is attached to the 5' end, and another is attached to an internal nucleotide, wherein said oligonucleotide primer is suitable for PCR amplification and melting curve analysis.

wherein the fluorophore and quencher (or another fluorophore) on said oligonucleotide primer may be less than 6 nucleotides apart, or less than 7 nucleotides apart, or less than 8 nucleotides apart, or less than 9 nucleotides apart, or less than 10 nucleotides apart, or less than 11 nucleotides apart, or less than 12 nucleotides apart, or less than 13 nucleotides apart, or less than 14 nucleotides apart, or less than 15 nucleotides apart.

The present invention further provides a reaction mixture, which comprises: a first primer and a second primer (or linked-second primer-probe) which are capable of amplifying a product comprising a sequence covering that of the diagnostic region of the target nucleic acid sequence via an amplification process, wherein the first primer comprises a sequence based on that of a first region of the target nucleic acid sequence (i.e. the first primer sequence is identical or substantially identical to the first region), wherein the first region overlaps the 5' part of the diagnostic region of the target nucleic acid sequence, but does not overlap the variant nucleotide(s), wherein the 3' end of the first region is adjacent to the 5' side of the variant nucleotide(s), wherein the first primer is not an allele-specific primer, wherein the second primer (or the 3' primer portion of the linked-second primer-probe) comprises a sequence based on that of a second region located downstream of the diagnostic region of the target nucleic acid sequence, alternatively, the first primer is an allele-specific (or variant-specific) primer, which comprises 3' terminus nucleotide complementary to the variant nucleotide, a blocking oligonucleotide, which is an unlabelled oligonucleotide with an unextendable 3' end or a labelled oligonucleotide probe (or the 5' probe portion of the linked-second primer-probe), having a sequence based on that of the diagnostic region of a reference target nucleic acid sequence having wild-type nucleotide(s) (also referred to as normal nucleotide(s)) therein, wherein the corresponding nucleotide(s) on the blocking oligonucleotide (or probe portion of linked primer-probe) is identical to the normal nucleotide(s) on the target nucleic acid sequence, such that hybridization of the blocking oligonucleotide probe (or probe portion) to the diagnostic region of said reference target nucleic acid sequence results in the formation of a first duplex having a first melting temperature ($T_m1$), hybridization of the blocking oligonucleotide probe (or probe portion) to the diagnostic region of the (mutated) target nucleic acid sequence containing variant nucleotide(s) results in the formation of a second duplex having a second melting temperature ($T_m2$), wherein the $T_m2$ is lower than the $T_m1$, wherein the values of $T_m1$ and $T_m2$ are obtainable experimentally or are calculated theoretically, and a DNA polymerase which may be a proof-reading DNA polymerase with 3' to 5' exonuclease activity.

The present invention further provides a composition, which comprises: a first primer and a second primer (or linked-second primer-probe) which are capable of amplifying a product comprising a sequence covering that of the diagnostic region of the target nucleic acid sequence via an amplification process, wherein the first primer comprises a sequence based on that of a first region of the target nucleic acid sequence (i.e. the first primer sequence is identical or substantially identical to the first region), wherein the first region overlaps the 5' part of the diagnostic region of the target nucleic acid sequence, but does not overlap the variant nucleotide(s), wherein the 3' end of the first region is adjacent to the 5' side of the variant nucleotide(s), wherein the first primer is not an allele-specific primer, wherein the second primer (or the 3' primer portion of the linked-second primer-probe) comprises a sequence based on that of a second region located downstream of the diagnostic region of the target nucleic acid sequence, alternatively, the first primer is an allele-specific (or variant-specific) primer, which comprises a 3' terminus nucleotide complementary to the variant nucleotide, and a blocking oligonucleotide probe, which is an unlabelled oligonucleotide with an unextendable 3' end or a labelled oligonucleotide probe (or the 5' probe portion of the linked-second primer-probe), comprising a moiety and having a sequence based on that of the diagnostic region of a reference target nucleic acid sequence having wild-type nucleotide(s) (also referred to as normal nucleotide(s)) therein, wherein the corresponding nucleotide(s) on the labelled oligonucleotide probe (or probe portion of linked primer-probe) is identical to the normal nucleotide(s) on the target nucleic acid sequence, such that hybridization of the blocking oligonucleotide probe (or probe portion) to the diagnostic region of said reference target nucleic acid sequence results in the formation of a first duplex having a first melting temperature ($T_m1$), hybridization of the blocking oligonucleotide probe (or probe portion) to the diagnostic region of the (mutated) target nucleic acid sequence containing variant nucleotide(s) results in the formation of a second duplex having a second melting temperature ($T_m2$), wherein the $T_m2$ is lower than the $T_m1$, wherein the values of $T_m1$ and $T_m2$ are obtainable experimentally or are calculated theoretically.

The present invention further provides a labelled oligonucleotide probe, which comprises a quencher label or a reporter label attached at a 3' end of the probe and a reporter label or a quencher label attached to the 5' end or to an internal nucleotide of the probe. The internal reporter label is generally less than 20 nucleotides away from the 3' end, or preferably less than 19 nucleotides away from the 3' end, or more preferably less than 18 nucleotides away from the 3' end, or more preferably less than 17 nucleotides away from the 3' end, or more preferably less than 16 nucleotides away from the 3' end, or more preferably less than 15 nucleotides away from the 3' end, or more preferably less than 14 nucleotides away from the 3' end, or more preferably less than 13 nucleotides away from the 3' end, or more preferably less than 12 nucleotides away from the 3' end, or more preferably less than 11 nucleotides away from the 3' end, or more preferably less than 10 nucleotides away from the 3' end. The internal reporter label may be less than 9 nucleotides away from the 3' end, or less than 8 nucleotides away from the 3' end, or less than 7 nucleotides away from the 3' end, or less than 6 nucleotides away from the 3' end, or less than 5 nucleotides away from the 3' end.

The present invention further provides a kit for determining whether a target nucleic acid sequence in a sample has variant nucleotide(s) in a diagnostic region thereof, comprising:

a first primer and a second primer (or linked-second primer-probe) which are capable of amplifying a product comprising a sequence covering that of the diagnostic region of the target nucleic acid sequence via an amplification process, wherein the first primer comprises a sequence based on that of a first region of the target nucleic acid sequence (i.e. the first primer sequence is identical or substantially identical to the first region), wherein the first region overlaps the 5' part of the diagnostic region of the target nucleic acid sequence, but does not overlap the variant nucleotide(s), wherein the 3' end of the first region is adjacent to the 5' side of the variant nucleotide(s), alternatively, the first primer is allele-specific (or variant-specific) primer, which comprises a 3' terminus nucleotide complementary to the variant nucleotide, wherein the second primer (or the 3' primer portion of the linked-second primer-probe) comprises a sequence based on that of a second region located downstream of the diagnostic region of the target nucleic acid sequence, and a blocking oligonucleotide probe, which is an unlabelled oligonucleotide with an unextendable 3' end or a labelled oligonucleotide probe (or the 5' probe portion of the linked-second primer-probe), comprising moiety(s), having a sequence based on that of the diagnostic region of a reference target nucleic acid sequence having wild-type nucleotide(s) (also referred to as normal nucleotide(s)) therein, wherein the corresponding nucleotide(s) on the blocking oligonucleotide probe (or probe portion of linked primer-probe) is identical to the normal nucleotide(s) on the target nucleic acid sequence, such that hybridization of the blocking oligonucleotide probe (or probe portion) to the diagnostic region of said reference target nucleic acid sequence results in the formation of a first duplex having a first melting temperature ($T_m1$), hybridization of the blocking oligonucleotide probe (or probe portion) to the diagnostic region of the (mutated) target nucleic acid sequence containing variant nucleotide(s) results in the formation of a second duplex having a second melting temperature ($T_m2$), wherein the $T_m2$ is lower than the $T_m1$, wherein the values of $T_m1$ and $T_m2$ are obtainable experimentally or are calculated theoretically.

In any above mentioned method, reaction mixture, composition or kit, the allele-specific first primer may be designed to comprise one or two or three non-match extra nucleotides, alternatively with one or two nucleotide deletions in the positions within six, five, four or three nucleotides from the 3' terminus. When this type of primer anneals to the primer binding site of a nucleic acid target in a sample, the hybridisation creates a bulge, which is either located on the primer (in the case of the extra unmatched nucleotides in the primer) or on the template (in the case of the nucleotide deletions in the primer). The 3'-terminal base of the first primer is complementary to the variant base being detected. This design results in an unmatched base bulge on the unmatched nucleotide positions but complementary 3' ends between the mutant-specific primer and the mutant template, which may cause efficient primer extension. However a double, or triple or more 3'-end mismatch between the mutant-specific primer and the wild-type template may inhibit primer extension. The mutation specific primer may comprise label(s), which can be used for monitoring amplification and for melting curve analysis. Depending on which nucleotide the label is attached to, the signal can increase or decrease when the primer is incorporated into an amplifed product. A very useful design is that the primer is attached with a fluorophore or quencher at the 5' end and at an internal nucleotide (FIG. 3F). The combinations can be 5' fluorophore-internal fluorophore, 5' fluorophore-internal quencher or 5' quencher-internal fluorophore.

If the first primer is not a mutation-specific primer, the 3' end of the first region substantially complementary (identical) to the first primer may abut the 5' side of at least one of the variant nucleotide(s) in the diagnostic region of the target nucleic acid sequence, such that when the annealed first primer is extended, the first extended nucleotide is the variant nucleotide.

In other embodiments, the 3' end of the first region may be spaced apart from the 5' of the variant nucleotide(s) by one to nine nucleotides, such that when the annealed first primer is extended, the second to tenth extended nucleotide(s) is the variant nucleotide.

The blocking oligonucleotide which may be a labelled oligonucleotide probe (or the 5' probe portion of the linked second primer-probe) or a plain unlabelled oligonucleotide with an unextendable 3' end may comprise naturally occurring nucleotides or modified nucleotides or linkages. The modified nucleotides or linkages may be selected from a group of LNA, PNA, d(2-am)ATP, 5-methylcytosine, minor groove binders, phosphorothioate linkage (S-Oligo) or base analogues.

The labelled oligonucleotide comprise moiety(s), which may include, but is not limited to fluorescent moiety, a non-fluoresecent dye, a quencher moiety, a photoluminescent moiety, a luminescent moiety or a chemiluminescent moiety.

The labelled oligonucleotide probe (or the 5' probe portion of the linked second primer-probe) may comprise a reporter label and a quencher label, wherein the quencher label is capable of quenching the fluorescence of said reporter label when said oligonucleotide probe is in a single-stranded conformation and is not hybridized to said target nucleic acid, wherein said oligonucleotide probe or the 5' probe portion of the linked second primer-probe is capable of forming a double stranded conformation when hybridized to said target nucleic acid, where the fluorescence of said reporter label is unquenched such that the fluorescence intensity of said reporter label is greater than the fluorescence intensity of said reporter label when said oligonucleotide probe is in a single stranded conformation not hybridized to said target nucleic acid.

The blocking oligonucleotide, which is labelled oligonucleotide probe or the 5' probe portion of the linked second primer-probe or a plain oligonucleotide with an unextendable 3' end may be divided into two portions. The first portion comprises a sequence identical to the 5' part sequence of the diagnostic region, and the second portion comprises a sequence identical to the 3' part sequence of the diagnostic region, wherein the first portion and second portion of the labelled oligonucleotide probe is contiguous, the 5' part and 3' part of the diagnostic region may not be contiguous. In other words, the blocking oligonucleotide may comprise extra non-match nucleotides or nucleotide deletions in the middle positions of the blocking oligonucleotide, such that when the blocking oligonucleotide hybridises to the diagnostic region of a nucleic acid target, the hybridisation creates an unpaired base bulge, which is either located on the blocking oligonucleotide (in the case of the extra unmatched nucleotides in the blocking oligonucleotide) or on the template (in the case of the nucleotide deletions in the blocking oligonucleotide). The extra non-match nucleotides or deletions may be one nucleotide, or two nucleotides, or three nucleotides, or four nucleotide, or five nucleotides, or more than 5 nucleotides.

The present invention also provides a method for multiplex detection of multiple mutations in a single closed tube. In a multiplex reaction, two pairs or more than two pairs of primers are used to amplify multiple target nucleic acid sequences. An endogenous gene may be amplified in the same reaction as an amplification control. The endogenous gene amplification control may be used as reference to determine if the mutant amplification is positive or negative, or used as normaliser to quantitate the target nucleic acid.

The probe of the present invention may be used in a homogeneous assay system wherein the detection and analysis of nucleic acid sequences are performed along with the amplification of a target nucleic acid. Alternatively, the probes of the invention may be used in end-point detection assays independent of target amplification.

Analysis may occur during amplification in a homogeneous assay system, which may involve real-time monitoring fluorescence signal cycle by cycle. Since the probe is not hydrolysed during amplification, the target nucleic acid may be studied through melting curve analysis subsequent to amplification.

(B) The labelled oligonucleotide contains a quencher (Q) at the 3' end, and the first primer may be an allele-specific primer. The reaction also contains a detector probe;
(C) The labelled oligonucleotide contains a fluorophore (F) at the 3' end, and the first primer may be an allele-specific primer;
(D) The labelled oligonucleotide contains a fluorophore (F) internally, and the first primer may be an allele-specific primer;
(E) The labelled oligonucleotide contains a quencher (Q) at the 3' end, the first primer contains a fluorophore (F) at the 5' end, and may be an allele-specific primer;
(F) The labelled oligonucleotide contains a Fluorophore (F) or a quencher (Q) at the 3' end, the first primer contains a fluorophore (F) or a quencher (Q) at the 5' end and at an internal nucleotide, and the first primer may be an allele-specific primer; and
(G) The blocking oligonucleotide without a label comprises nucleotide deletions in the middle positions of the blocking oligonucleotide, when the blocking oligonucleotide hybridises to the diagnostic region of a nucleic acid target, the hybridisation creates unpaired base bulge.

Figure 4:
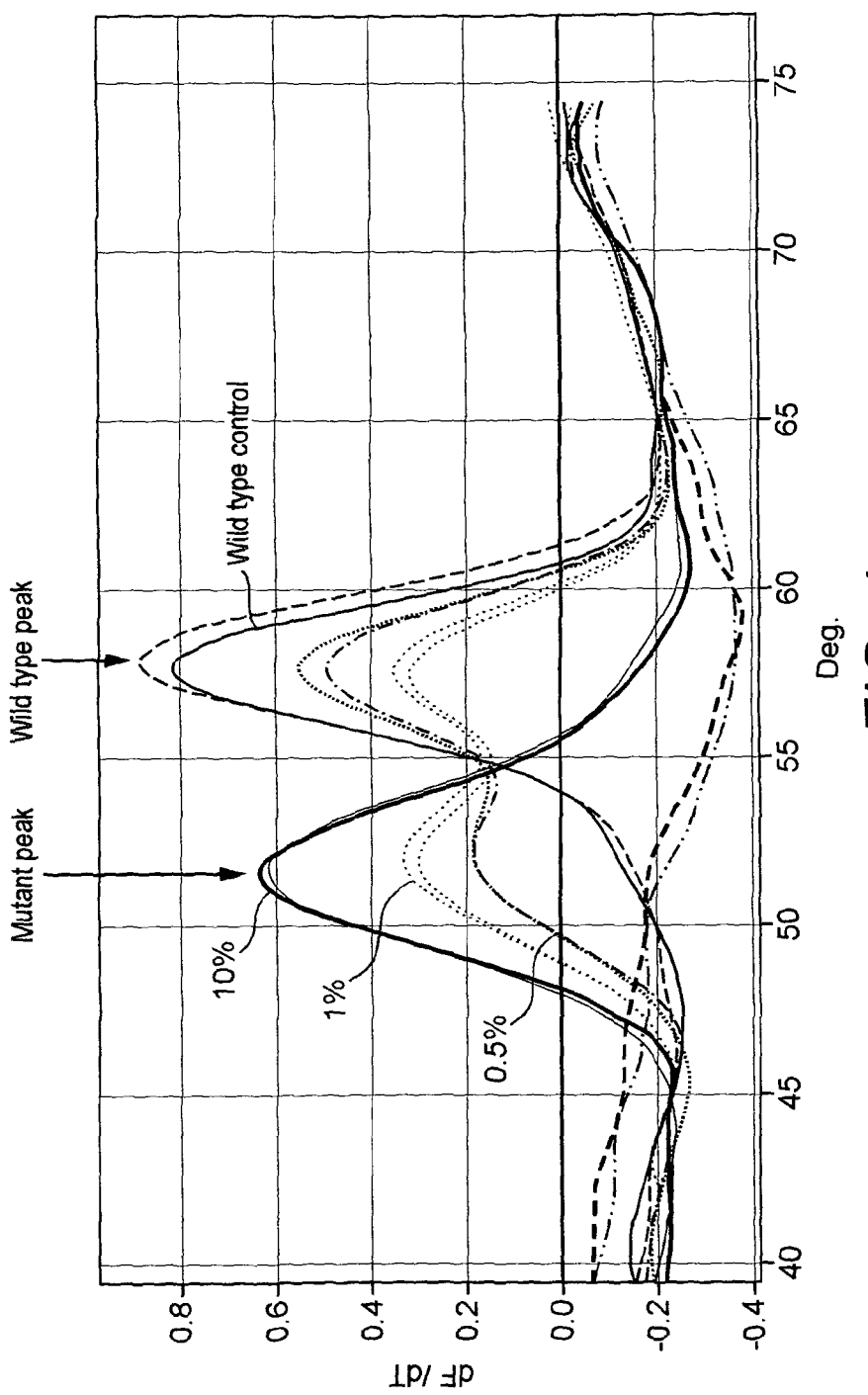

FIG. 4 melting curve analysis of EGFR exon 21 mutation L858R on serial dilutions of mutated DNA in wild type DNA background.

The invention will now be further described with reference to the following non-limiting examples. Other embodiments of the invention will occur to those skilled in the art in light of these.

The disclosure of all references cited herein, in as much as they may be used by those skilled in the art to carry out the invention, are hereby specifically incorporated herein by cross-reference.

EXAMPLE 1

EGFR (Epidermal Growth Factor Receptor) signalling pathway causes cell growth and proliferation via several signalling molecules, including KRAS and BRAF. Oncogenic mutations in these genes may cause cancer. Recent evidence indicates that the presence of epidermal growth factor receptor (EGFR) or KRAS mutations in non-small cell lung cancer (NSCLC) can predict the response of the tumour to drugs such as gefinitib.

In this example, the point mutation L858R in EGFR exon 21 was chosen as a model mutation site to test this technique. Primers and probes were designed to amplify a region containing the mutation site. The forward primer has a 3' terminus nucleotide right before the mutation site, not overlapping the L858R nucleotide, i.e. the forward primer is not an allele-specific primer. The sequences of forward primers and reverse primers are listed in Table 1. The 5' part of the probe overlaps some sequence of the forward primers, and its 3' part contains sequence covering the mutation site (matching the wild type sequence). The sequence of probe is also listed in Table 1. The probe contains fluorophore Fam at its 5' end and black quench dye BHQ1 at the 3' end.

TABLE 1

EGFR exon21 L858R, sequences of primers and probe

| number | name | sequence (5'-3') | length (bp) |
|---|---|---|---|
| SEQ ID NO. 1 | EGFR21forward1 | GATCACAGATTTTGGGC | 17 |
| SEQ ID NO. 2 | EGFR21forward2 | AGATCACAGATTTTGGGC | 18 |
| SEQ ID NO. 3 | EGFR21reverse1 | CTTTGCCTCCTTCTGCATGGTA | 22 |
| SEQ ID NO. 4 | EGFR21reverse2 | CTCCTTACTTTGCCTCCTTCTGCA | 24 |
| SEQ ID NO. 5 | EGFR21probe | GATCACAGGTTTTGCTGGCAAACTGC | 26 |

Preparation of Templates

A DNA fragment containing the L858R EGFR exon21 was synthesised and cloned into a vector. The mutated plasmid DNA is mixed with wild type human genomic DNA such that the concentrations of mutated DNA are 10%, 1%, 0.5%. The wild type DNA is 3000 copies/μl.

PCR Reaction

PCR mixture was prepared as listed in Table 2. Every PCR run included water control and wild type DNA control. Normal Taq polymerase or hot-start Taq polymerase was used. In some experiments, DNA polymerase with proof-reading activity such as PWO DNA polymerase and probe with the 3' end modified to be resistant to 3' exonuclease activity of the DNA polymerase were used. It was found that the use of DNA polymerase with proof-reading activity gave good results, which showed increased sensitive of detection of mutations.

TABLE 2

| PCR mixture | |
|---|---|
| Composition | Final concentration |
| PCR Buffer | 1× |
| dNTPs | 0.1 mM |
| EGFR21 forward primer | 0.05 μM |
| EGFR21reverse primer | 0.2 μM |
| EGFR21probe | 0.25 μM |
| Polymerase | 0.4 U |
| $H_2O$ | appropriate |
| DNA template | 1 μl |
| Total volume | 20 μl |

PCR Condition

A PCR program was set up as set out in Table 3. Fam signal collection was carried out on annealing step 50° C.:

TABLE 3

| PCR program | | | |
|---|---|---|---|
| step | temperature | duration | cycles |
| 1 | 95° C. | 1 min | 1 |
| 2 | 93° C. | 3 sec | 50 |
| 3 | 56° C. | 20 sec | |
| 4 | 53° C. | 20 sec | |

TABLE 3-continued

PCR program

| step | temperature | duration | cycles |
|---|---|---|---|
| 5 | 50° C. | 20 sec | |
| 6 | 72° C. | 6 sec | |
| 7 | 95° C. | 30 sec | 1 |
| 8 | Melting curve: 39-75° C., every time increase 1° C., hold 5 sec, collection of FAM fluorecence signals. | | |

When PCR finished, the melting curve was performed. The wild type DNA gave a melting peak at 57° C., whereas the mutated DNA gave a melting peak at 51° C. In the case where the PCR tubes contained the 1% and 0.5% mutated DNA, both peaks were seen.

EXAMPLE 2

Figure 1:
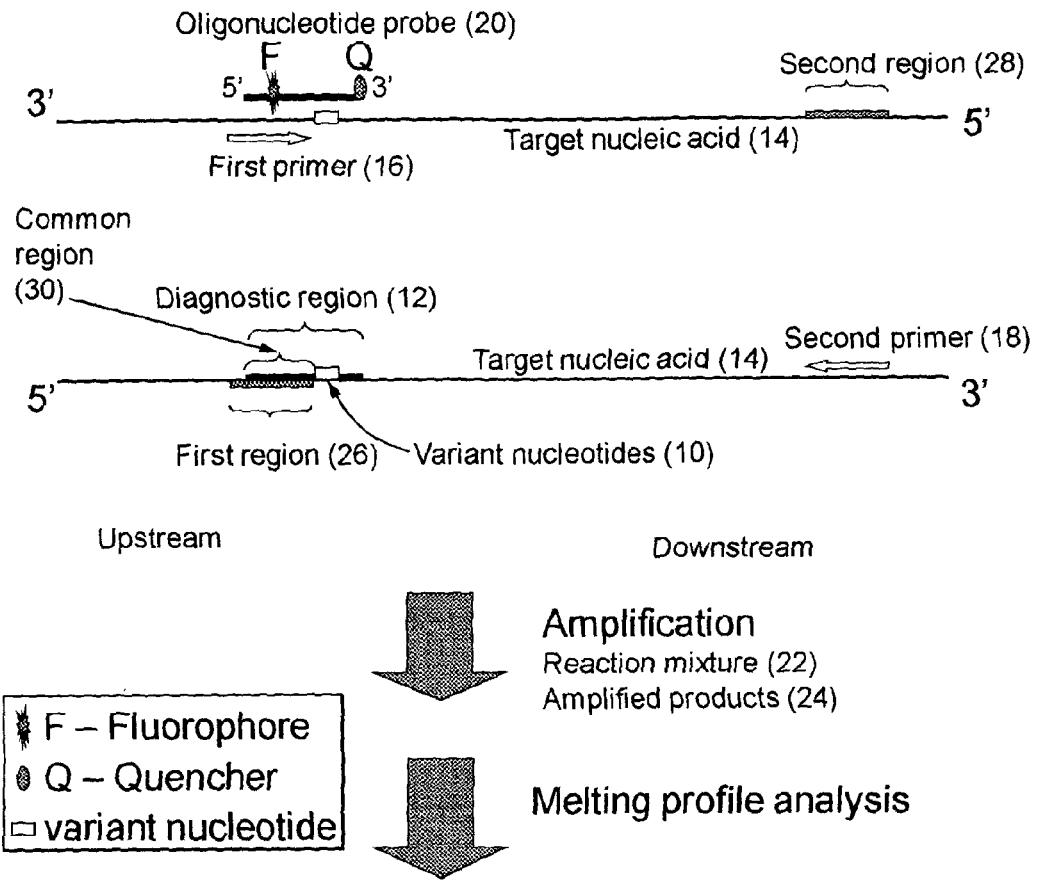
FIG. 1 depicts a schematic of an illustrative embodiment of one aspect of the present invention. Components include the following: first primer (16), second primer (18) and blocking oligonucleotide probe (20). On cooling, both blocking labelled oligonucleotide probe and first primer compete to bind the same site of amplicons, enriching the mutated target sequence (14). Melting of the probe element provides targeted genotyping, where high Tm peak indicates wild type sequence; low Tm peak indicates mutated sequence.
Figure 1:
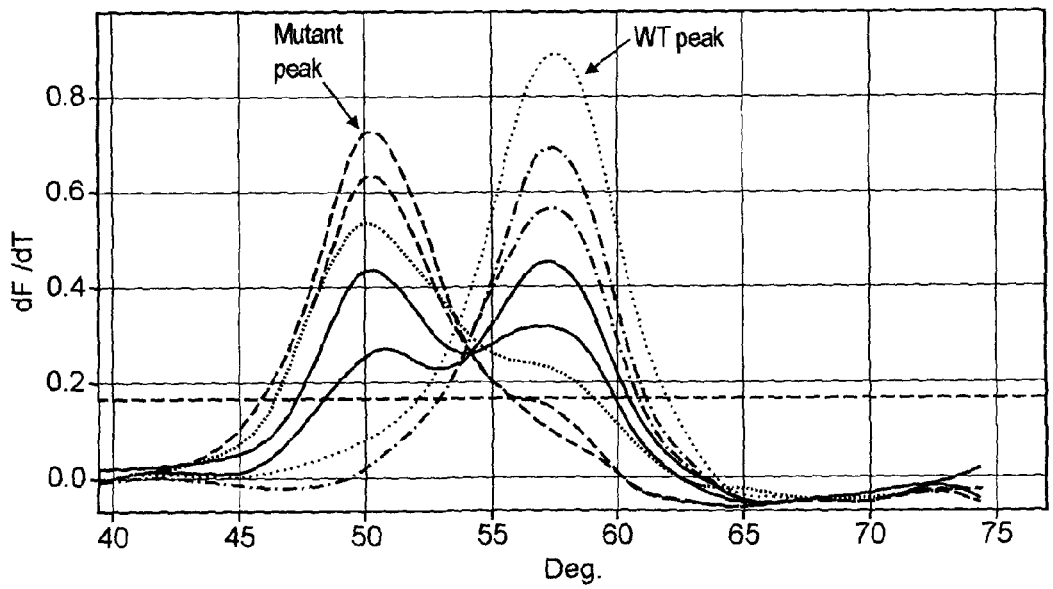
Figure 2:
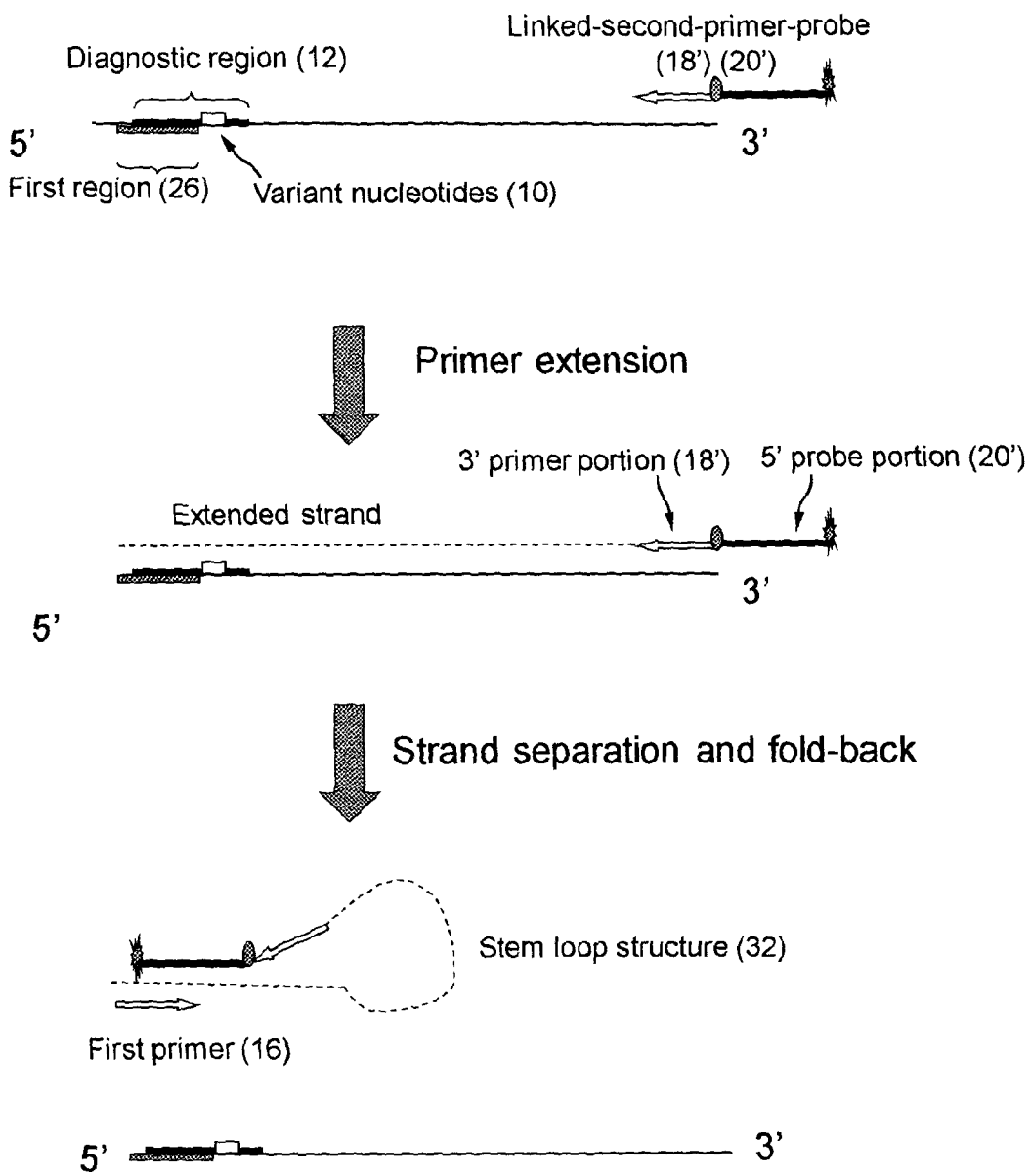
FIG. 2 The linked-second primer-probe (18'; 20') is an amplification primer that includes a tail as a labelled probe element that is complementary to the extension product of the primer. On cooling, an intra-molecular stem-loop (32) of the excess linked-primer-probe strand is formed. The 5' labelled probe element matches to the wild type so that the stem-loop is strongly formed. However, a 1-bp or more mis-match exists between the probe element and the mutant allele. During PCR amplification, the first primer is hybridised to the destabilized mutant stem, but wild-type extension is blocked, leading to enrichment of the mutant allele.
Figure 3:
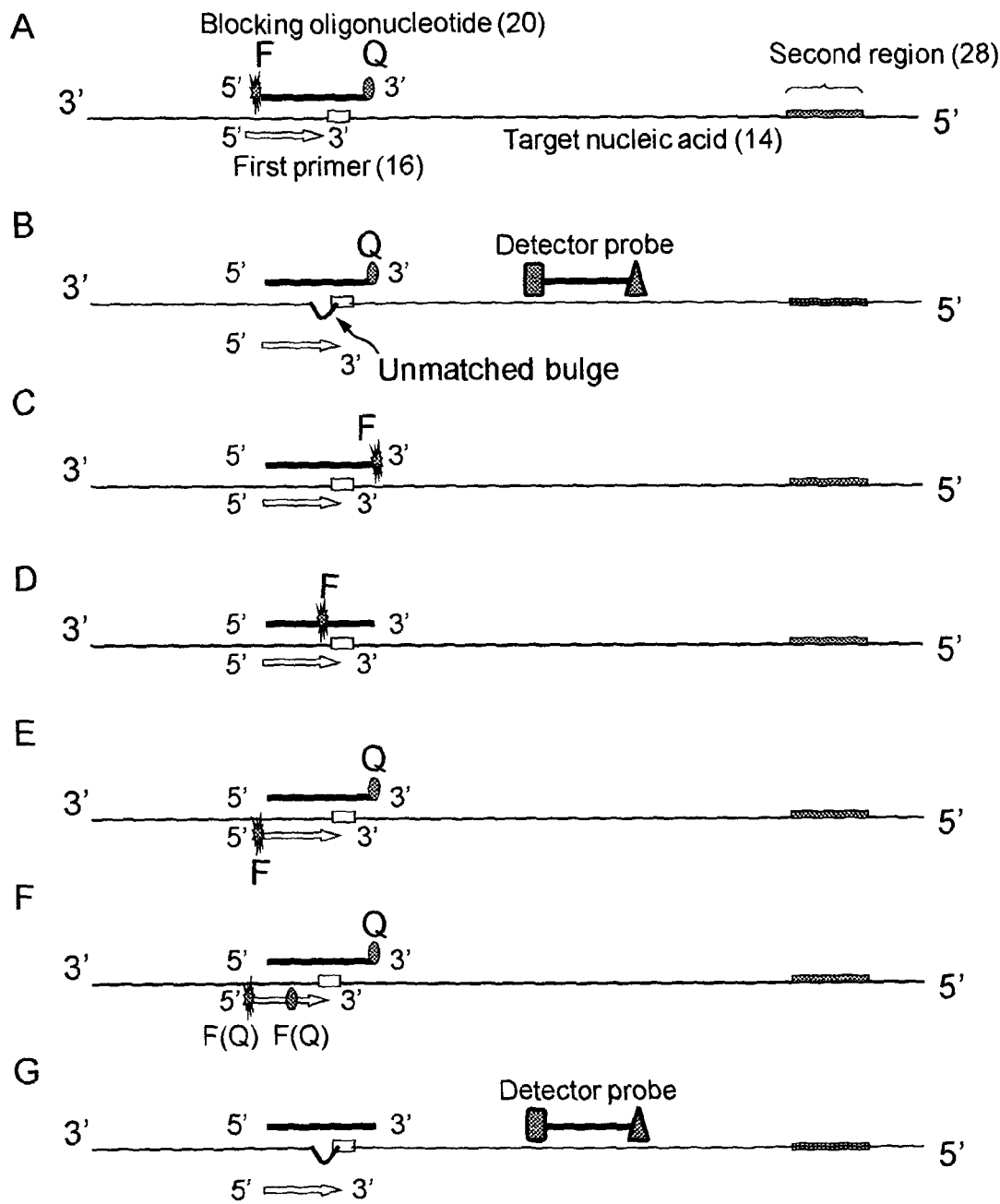
FIG. 3A-G depicts various labels on blocking labelled oligonucleotides and first primers.
(A) The labelled oligonucleotide contains a fluorophore (F) and quencher (Q) at the 5' end and 3' end. The first primer is not labelled and may be not an allele-specific primer.

In Example 1, the labelled oligonucleotide probe and second primer are separate molecules, i.e. they are not linked. In this example, a linked-primer-probe was used in which the labelled oligonucleotide and the second primer (the reverse primer) are linked together, i.e. they are linked to become a single oligonucleotide (FIG. 2).

For detecting EGFR exon21 point mutation L858R, the linked-primer-probe, had a sequence:

SEQ ID NO 6.
5'ttGATCACAGGTTTTGCTGGCAAACTGCCTTTGCCTCCTTCTGCATG
GTA-3'

It comprises a 5' probe portion and a 3' primer portion. The sequence of 3-28 nucleotides is the probe portion, the 26th nucleotide dT is attached with quencher BHQ1. The last 22 nucleotides (3' part) is the primer portion, serving as primer. The first two nucleotides tt are introduced to mismatch the target sequence. The 5' end of the linked-primer-probe is attached with fluorescent dye Fam.

The probe portion in linked-primer-probe matches the wild-type target sequence, which hybridizes to the diagnostic region of the extended strand and blocks hybridisation of the first primer (the forward primer) with the stem part of the secondary structure and limits formation of the full-length PCR product (FIG. 2), A 2-bp mismatch at the 5' end probe portion of the linked-primer-probe is included to prevent 3'-end extension of the stem-loop of the first primer extended strand that may form from the full-length single strand. In this example, the 5' probe portion and 3' primer portion may be linked by normal nucleotide(s), so that polymerase can copy the whole linked primer-probe.

PCR condition and cycling program were set up as per Example 1.

EXAMPLE 3

Kras codon 12 and 13 mutation detection.
The allele-specific primers are:

SEQ ID NO. 7
5' Fam-caaTGGTAGTTGGAGCTGT-3';

SEQ ID NO. 8
5'-gtgtTGTGGTAGTTGGAGCTGT-3'
(Fam-dT at second nucleotide from the 5' end);

SEQ ID NO. 9
5' Fam-tcaGTGGTAGTTGGAGCTT-3'
(dabcyl-dT at the 9$^{th}$ nucleotide from the 5'end);

SEQ ID NO. 10
5' Fam-caaTGGTAGTTGGAGCTC-3';

SEQ ID NO. 11
5' Cy5-caGaGGTAGTTGGAGCTGA-3';

SEQ ID NO. 12
5' cy5-acaGTGGTAGTTGGAGCTA-3';

SEQ ID NO. 13
5' Fam-aacGaTAGTTGGAGCTGGTGA-3'
(dabcyl-dT at 10$^{th}$ nucleotide from the 5' end);

SEQ ID NO. 14
5' Fam-caaaGGTAGTTGGAGCTGC-3';

SEQ ID NO. 15
5' Fam-TAAGTTGTGGTAGTTGGAGCTGT
(Fam-dT at the 8$^{th}$ nucleotide from the 5' end);

SEQ ID NO. 16
5' Dabcyl-taagGTAGTTGGAGCTGGTGA
(Fam-dT at the 9$^{th}$ nucleotide);.

The reverse primer is:

SEQ ID NO. 17
5'TTACCTCTATTGTTGGATCATATTC-3';.

The labelled oligonucleotide probe (blocking probe) is:

SEQ ID NO. 18
5' Fam- TGGTAGTTGGCTGGTGGCG-BHQ1-3';
or

SEQ ID NO. 19
5'- GGTAGTTGGATGGTGGCG-BHQ1 3';.

The detector probe (dual labelled TaqMan probe) is:

SEQ ID NO. 20
5' Hex- taggcaagagtgccttgacga-BHQ1 3'.

Each assay reaction mixture (20 ul total) contained 1× TaqMan Gene Expression master mixture (applied Biosystems, PN 4333458N), 0.5 ng/ul genomic DNA, 50 nM allele-specific primer, 200 nM TaqMan probe, 500 nM reverse primer, 500 nM blocking probe. The reactions were incubated in 96-well plate at 95° C. for 10 minutes, then for 10 cycles at 95° C. for 10 seconds, 51° C. for 40 second and 72° C. for 20 seconds, then for 50 cycles at 95° C. for 10 seconds, 56° C. for 30 second and 60° C. for 30 seconds. Following PCR, a melting protocol from 50° C. to 92° C. was used. All reactions were run in duplicate in Stratagene MX3005P real time PCR machine. Assays were performed using general experimental design and reaction conditions indicated above. Singleplex, doubleplex and tripleplex for detecting one mutation, two mutations and three mutations were performed in a single closed tube reaction. Real-time monitoring of the fluorescent emission was used to determine the Ct value; while melting curve analysis was used to determine which mutation is present in the targeted DNA.

The allele-specific primer may be labelled with a fluorophore at the 5' end alone, for example primers SEQ ID NO. 7, SEQ ID NO. 8 (Fam-dT at second nucleotide).

When the allele-specific primer SEQ ID NO. 7 is incorporated into a PCR product, the fluorescent signal is decreased. When the allele-specific primer (SEQ ID NO. 8) (Fam-dT at the second nucleotide) is incorporated into a PCR product, the fluorescent signal is increased. The allele-specific primer may be labelled with a fluorophore at the 5' end and a quencher (dabcyl or BHQ) at an internal nucleotide, for example primer SEQ ID NO. 9 (dabcyl-dT at the nucleotide 9), which, when incorporated into a PCR product, results in an increased fluorescent signal. Similarly, the allele-specific primer may be labelled with a fluorophore at the 5' end and a same or different fluorophore at an internal nucleotide, for example primer SEQ ID NO. 15 (5' end-Fam, Fam-dT at the nucleotide 8), which, when incorporated into a PCR product, results in an increased fluorescent signal.

The allele-specific primer may be labelled with a quencher at the 5' end and a fluorophore at an internal nucleotide, for example primer SEQ ID NO. 16 (5' end dabcyl, Fam-dT at nucleotide 9), which, when incorporated into a PCR product, results in an increased fluorescent signal The allele-specific primer, when incorporated into a PCR product, results in an increased or decreased fluorescent signal, which can be monitored in real-time during PCR, or can be used for melting curve analysis. The amplification curve and/or melting profile can be used to determine which nucleotides (variant or normal) are present in a target nucleic acid.

The reaction may contain a detector probe, which can be a TaqMan probe. In this example the detector probe is HEX-BHQ1 dual labelled oligonucleotide (SEQ ID NO. 20). A reaction may contain both detector probe and labelled allele-specific primers, which both can be monitored in real time during PCR but only the labelled allele-specific primer, when incorporated into a PCR product, can be used for melting curve analysis.

The reaction may contain another labelled oligonucleotide probe (also known as blocking probe). The blocking probe functions as blocker to prevent wild type sequence being amplified. The blocking probe competes with allele-specific primer for the binding site, which binds to blocking probe more strongly. The labels on the blocking probe may be fluorescent or non-fluorescent dyes. The blocking oligonucleotides (SEQ ID NO. 18) or (SEQ ID NO. 19 contain labels Fam and/or BHQ1 at the 5' end and 3' end, which increase the Tm of the labelled oligonucleotide in comparison with the oligonucleotide without label.

EXAMPLE 4

Detection of EGFR exon 21 mutations L858R and L861Q, exon 20 mutation T790M

The mutation-specific primer for L858R has a sequence

SEQ ID NO. 21
5'-CAAGATCACAGATTTTGGCG-3' which was designed to have a nucleotide "G" deletion within five nucleotides from the 3' end.

The mutation-specific primer for L861 QR has a sequence

SEQ ID NO. 22
5'-GATTTTGGGCTGGCCAACA-3' which was designed to have a nucleotide "A" deletion within five nucleotides from the 3' end.

The reverse primer has a sequence:

SEQ ID NO. 23
5'-CTTACTTTGCCTCCTTCTGCA-3'.

The mutation-specific primer for EGFR exon 20 mutation T790M has a sequence:

SEQ ID NO. 24
5'-CCGAAGGGCATGAGCTCA-3' which was designed to have a nucleotide "G" deletion within three nucleotides from the 3' end.

Blocking oligonucleotide for detecting EGFR exon 21 mutations L858R and L861Q were designed to have a sequence:

SEQ ID NO. 25
5'-GATCACAGgTTTTGCTGGCAAACTGc-3'-Ph in which the 3' end is blocked by a phosphate group. PCR conditions were the same as described in Example 3. The results showed that these primers, with nucleotide deletions in the 3' ends, were more specific than the primers without nucleotide deletions.

The following passages are provided as clauses and are not to be considered as claims:

1. A method for determining the presence or absence of variant nucleotide(s) in a diagnostic region of a target nucleic acid sequence in a sample, comprising:

(a) providing a first primer and a second primer which are capable of amplifying a product comprising a sequence covering that of the diagnostic region of the target nucleic acid sequence via a PCR process, wherein the first primer comprises a sequence based on that of a first region of the target nucleic acid sequence (i.e. the first primer sequence is identical or substantially identical to the first region), wherein the first region overlaps the 5' part of the diagnostic region of the target nucleic acid sequence, but does not overlap the variant nucleotide(s), wherein the 3' end of the first region is adjacent to the 5' side of the variant nucleotide(s), wherein the second primer comprises a sequence based on that of a second region located downstream of the diagnostic region of the target nucleic acid sequence, providing a labelled oligonucleotide probe comprising a detectable moiety and having a sequence based on that of the diagnostic region of a reference target nucleic acid sequence having no variant nucleotide(s) (also referred to as normal nucleotide(s)) therein, wherein the corresponding nucleotide(s) on the labelled oligonucleotide is identical to the normal nucleotide(s) on the target nucleic acid sequence, such that hybridization of the labelled oligonucleotide probe to the diagnostic region of said reference target nucleic acid sequence results in the formation of a first duplex having a first melting temperature ($T_m1$), hybridization of the labelled oligonucleotide probe to the diagnostic region of the (mutated) target nucleic acid sequence containing variant nucleotide(s) results in the formation of a second duplex having a second melting temperature ($T_m2$), wherein the $T_m2$ is lower than the $T_m1$, wherein the values of $T_m1$ and $T_m2$ are obtainable experimentally or are calculated theoretically;

(b) carrying out an amplification reaction on a reaction mixture using nucleic acid polymerase, the labelled oligonucleotide probe and the pair of the first and second primers with a nucleic acid sample under conditions which are permissive for the PCR process; and (c) subjecting the PCR products to a melting profile analysis to determine melting temperatures of the labelled oligonucleotide probe hybridised to the PCR products, wherein the presence of the second melting temperature(s) of the second duplex in the melting profile analysis is indicative of the presence of the variant nucleotide(s) in the diagnostic region of the target nucleic acid sequence contained in the nucleic acid sample.

2. The method according to claim 1, wherein said PCR uses slow ramping rates or multiple annealing temperatures.

3. The method according to claim 2, wherein said slow ramp rate is lower than 2° C./sec, or is lower than 1° C./sec, or is lower than 0.5° C./sec, or is lower than 0.2° C./sec.

4. The method according to claim 2, wherein said PCR process includes a series of multiple annealing temperatures in each cycle of the PCR thermal program, wherein said multiple annealing temperatures run in a sequence from the middle temperature to the lowest annealing temperature or from the lowest annealing temperature to the extension temperature within each thermal cycle.

5. The method according to claim 1, wherein 3' end of the first region abuts the 5' of at least one of the variant nucleotide(s) in the diagnostic region of the target nucleic acid sequence, wherein when the annealed first primer is extended, the first extended nucleotide is the variant nucleotide.

6. The method according to claim 1, wherein 3' end of the first region is spaced apart from the 5' of the variant nucleotide(s) by one to nine nucleotides, wherein when the annealed first primer is extended, second to tenth extended nucleotide(s) is the variant nucleotide.

7. The method according to claim 1, wherein the first primer, capable of hybridising to the target nucleic acid sequence, has a melting temperature which is the same or similar to the second melting temperature, or has a melting temperature which is in the range of the second melting temperature minus three to the second melting temperature plus three ($T_{m2}-3$ to $T_{m2}+3$).

8. The method according to claim 1, wherein said labelled oligonucleotide probe comprises naturally occurring nucleotides.

9. The method according to claim 1, wherein said labelled oligonucleotide probe comprises modified nucleotides or linkages.

10. The method according to claim 9, wherein said modified nucleotides or linkages comprise LNA, PNA, d(2-amA)TP, 5-methylcytosine, minor groove binders, or base analogues.

11. The method according to claim 1, wherein the moiety is a fluorescent moiety, a photoluminescent moiety, a luminescent moiety, or a chemiluminescent moiety.

12. The method according to claim 1, wherein said labelled oligonucleotide probe comprises a reporter label and a quencher label, wherein the quencher label is capable of quenching the fluorescence of said reporter label when said oligonucleotide probe is in a single-stranded conformation and is not hybridized to the target nucleic acid, wherein said oligonucleotide probe is capable of forming a double stranded conformation when hybridized to said target nucleic acid, where the fluorescence of said reporter label is unquenched such that the fluorescence intensity of said reporter label is greater than the fluorescence intensity of said reporter label when said oligonucleotide probe is in a single stranded conformation not hybridized to the target nucleic acid, wherein the quencher label is attached to the 3' end of the probe, the reporter label is attached to the 5' end of the probe or reporter label is attached to a internal nucleotide of the probe.

13. The method according to claim 1, wherein said labelled oligonucleotide probe is divided into two portions, first portion comprising sequence substantially identical to the 5' part sequence of the diagnostic region, and second portion comprising sequence substantially identical to the 3' part sequence of the diagnostic region, wherein the first portion and second portion of the labelled oligonucleotide probe are contiguous, the 5' part and 3' part of the diagnostic region are not contiguous.

14. The method according to claim 1, wherein the labelled oligonucleotide and second primer is linked together, i.e. they are linked to become a single oligonucleotide, wherein the labelled oligonucleotide probe is attached at 5' end of the second primer, wherein the linked-primer-probe acts as primer and initiates extension on the template, the probe portion in the linked-primer-probe on the extended strand folds back and hybridise with its extended strand, creating a stem-loop structure, the 5' probe portion in linked-primer-probe is mismatched to the mutated target sequence, destabilizing the stem-loop structure and allowing the primer to hybridize to the stem part of the secondary structure and complete the extension of the full-length PCR product, the probe portion in linked-primer-probe is matched to the wild-type target sequence, blocking primer hybridization with the stem part of the secondary structure and limiting formation of the full-length PCR product.

15. A labeled oligonucleotide probe for assaying a target nucleic acid sequence in a sample, comprising: a reporter label and a quencher label, which is capable of quenching the fluorescence of said reporter label when said oligonucleotide probe is in single-stranded conformation and is not hybridized to a target nucleic acid, wherein said oligonucleotide probe is capable of forming a double stranded conformation when hybridized to the target nucleic acid, where the fluorescence of said reporter label is unquenched such that the fluorescence intensity of said reporter label is greater than the fluorescence intensity of said reporter label when said oligonucleotide probe is in single stranded conformation not hybridized to the target nucleic acid, wherein said quencher label is non-fluorescent label, which is attached to the 3' terminus of the oligonucleotide probe, wherein said reporter label is fluorescent dye label, which is attached to an internal residue of the oligonucleotide probe, wherein the internal reporter label is less than 16 nucleotides away from 3' end, or is less than 15 nucleotides away from 3' end, or is less than 14 nucleotides away from 3' end, wherein said oligonucleotide probe is not suitable for hydrolysis probe-based real-time PCR.

The invention claimed is:

1. A method for determining the presence or absence of a variant nucleotide(s) in a diagnostic region of a target nucleic acid sequence in a sample, comprising:
  (a) providing a variant specific first primer and a second primer which are capable of amplifying a product comprising a sequence covering that of the diagnostic region of the target nucleic sequence via an amplification process, wherein the variant specific first primer is identical or substantially identical to a first region, the first region overlaps the 5' part of the diagnostic region of the target nucleic acid sequence, and the 3' end of the first region overlaps the variant nucleotide(s), and in which the variant specific first primer comprises a 3' terminus nucleotide complimentary to the variant nucleotide(s), and the second primer comprises a sequence based on that of a second region located downstream of the diagnostic region of the target nucleic acid sequence, wherein
  (i) the variant specific first primer comprises one, two, three or more non-match extra nucleotides compared to the sequence of the first region or one, two, three or more nucleotide deletions compared to the sequence of the first region, and in the positions within ten to three nucleotides from the 3' terminus of the variant specific primer, such that when the variant specific primer anneals to the primer binding site of a nucleic acid target, the hybridization creates an unpaired base bulge, which is either located on the primer in case of the extra unmatched nucleotides in the variant specific primer or on a template in the case of the nucleotide deletions in the variant specific primer;

and/or (ii) an oligonucleotide probe which acts as a blocker is provided, said oligonucleotide probe having a sequence based on that of the diagnostic region of the target nucleic acid sequence having no variant nucleotide(s) therein, wherein the blocking oligonucleotide and the variant specific first primer compete in binding to the same area of the target nucleic acid sequence, where the oligonucleotide probe comprises non-match extra nucleotides or nucleotide deletions in middle positions of the oligonucleotide probe compared to the sequence of the diagnostic region, such that when the oligonucleotide probe hybridises to the diagnostic region of a nucleic acid target hybridisation creates an unpaired base bulge, which is either located on the oligonucleotide probe in the case of the extra unmatched nucleotides in the oligonucleotide probe or on the template in the case of the nucleotide deletions in the oligonucleotide probe, and optionally providing a detector probe which is capable of hybridizing to the amplified target sequence, (b) carrying out an amplification reaction on a reaction mixture comprising the target nucleic acid using a nucleic acid polymerase, the blocking oligonucleotide probe, optionally a detector probe and the pair of the first and second primers under conditions which are permissive for the amplification process; and (c) detecting the amplified products by a melting profile analysis to determine the presence of the variant nucleotide(s) in the diagnostic region of the target nucleic acid sequence where the variant specific first primer comprises a label or by a change in a detectable signal where the reaction comprises the detector probe.

2. A method as claimed in claim 1 wherein the blocking oligonucleotide comprises moiety(s) which are attached to the 3' end and/or the 5' end of the blocking oligonucleotide, and is capable of increasing the melting temperature of the blocking oligonucleotide in comparison of a plain oligonucleotide without a moiety.

3. A method as claimed in claim 2 wherein the moiety is a fluorophore or a quencher.

4. A method as claimed in claim 1, wherein the amplification reaction comprises a plurality of first primers for multiplex detection of multiple variant nucleotide sequences, wherein different first primers comprise different labels or the same label in different sequence context, and in which the label may increase or decrease the detection signal when the first primers are incorporated into the amplified products compared to when the first primers are not incorporated into the amplified products, wherein the variant specific first primer is attached with a fluorophore at the 5' end and with a quencher at an internal nucleotide, or the first primer is attached with a quencher at the 5' end and with a fluorophore at an internal nucleotide or the first primer is attached with a fluorophore at the 5' end and with a same or different fluorophore at an internal nucleotide, such that when the primer is incorporated into the amplified product, the fluorescent signal is increased compared to when the primer is not incorporated into the amplified product, and the amplified product is capable of being analysed by melting curve analysis.

* * * * *